United States Patent [19]
Pamukcu et al.

[11] Patent Number: 5,948,911
[45] Date of Patent: Sep. 7, 1999

[54] METHOD FOR INHIBITING NEOPLASTIC CELLS AND RELATED CONDITIONS BY EXPOSURE TO THIENOPYRIMIDINE DERIVATIVES

[75] Inventors: Rifat Pamukcu, Spring House; Gary Piazza, Doylestown, both of Pa.

[73] Assignee: Cell Pathways, Inc., Horsham, Pa.

[21] Appl. No.: 09/196,205

[22] Filed: Nov. 20, 1998

[51] Int. Cl.⁶ .................................................. C07D 491/00
[52] U.S. Cl. .............................................................. 544/278
[58] Field of Search ............................................... 544/278

[56] References Cited

U.S. PATENT DOCUMENTS 5,869,486  2/1999  Lee et al. ................................ 514/248

*Primary Examiner*—Johann Richter
*Assistant Examiner*—Joseph Murray
*Attorney, Agent, or Firm*—Robert W. Stevenson

[57] ABSTRACT

A method for inhibiting neoplastic cells and related conditions by exposing them to substituted thienopyrimidine compounds.

19 Claims, No Drawings

METHOD FOR INHIBITING NEOPLASTIC CELLS AND RELATED CONDITIONS BY EXPOSURE TO THIENOPYRIMIDINE DERIVATIVES

TECHNICAL FIELD

This invention relates to a method for the inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps that can usually be removed leaving the colon intact. By contrast, polyposis syndrome cases can be characterized by many (e.g. hundreds or more) of polyps—covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds of that are useful in the methods of this invention include those of Formula I:

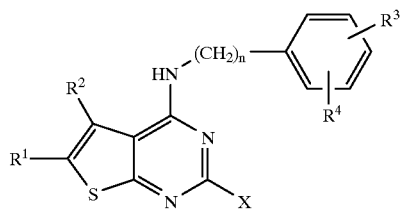

(I)

wherein $R_1$ and $R_2$ are independently selected from the group consisting of hydrogen, A, OA, alkenyl, alkynyl, $—NO_2$, $—CF_3$ or halogen, with the proviso that one of $R_1$ or $R_2$ is not hydrogen; or $R_1$ and $R_2$ together form a $C_{3-5}$ alkylene group;

$R_3$ and $R_4$ are independently selected from the group consisting of hydrogen, A, —OA, halogen, $—NO_2$, $—NH_2$, —NHA or —NAA'0, or $R_3$ and $R_4$ are together form a moiety selected from the group consisting of —O—CH$_2$—CH$_2$—, —O—CH$_2$—O— or —O—CH$_2$—CH$_2$—O, X is selected from the group consisting of a substituted 5–7 membered saturated heterocyclic ring or a substituted saturated or saturated isocyclic ring, wherein the substitutents on the "X" ring are one or two selected from the group consisting of —COOH, —COOA, —CONH$_2$, —CONAA', —CONHA, —CN, —CH$_2$COOH or —CH$_2$CH$_2$COOH;

A and A' are independently selected from the group consisting of hydrogen or $C_{1-6}$ alkyl; and n is 0, 1, 2 or 3; and physiologically acceptable salts thereof.

DETAILED DESCRIPTION OF THE INVENTION

The present invention also is a method of treating a patient with such lesions by administering to a patient a pharmacologically effective amount of a pharmaceutical composition that includes a compound of Formula I, wherein $R_1$ etc. are as defined above. Preferably, this composition is administered without therapeutic amounts of an NSAID.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_7$ and Y are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

As used herein, the term "halogen" means fluorine, chlorine, bromine, or iodine.

Compounds useful in the practice of this invention may be formulated into pharmaceutical compositions together with pharmaceutically acceptable carriers for oral administration in solid or liquid form, or for rectal or topical administration, although carriers for oral and parenteral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

When the present invention is used as a medicine for such diseases, it is administered by oral administration or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth.

In general the compounds useful in the practice of this invention are administered preferably in dosages between 1 and 500 mg, in particular between 5 and 100 mg per dosage unit. The daily dosage is preferably between approximately 0.02 and 10 mg/kg body weight. The specific dosage for each patient depends on various factors, e.g., on the efficacy of the used specific compound, on the age, the body weight, general health, gender, nutrition, the application time and method, elimination velocity, the pharmaceutical combination and the gravity of the respective disease for which the treatment is meant. Oral administration is preferred.

A and A' are independently preferably alkyl with 1–6 carbon atoms. In the preceding formulae "alkyl" can be linear, branched or cyclic, but preferably linear with 1–6 carbons and more preferably 1–5 carbons, most preferably methyl, ethyl or propyl, However, isopropyl, butyl, isobutyl, butyl or tert.-butyl, n-pentyl, neopentyl or isopentyl can be employed.

"Alkylene" is preferably linear and is most preferred propylene, butylene or pentylene.

Of the substituents $R_1$ and $R_2$, one is preferably hydrogen, while the other is preferably propyl or butyl, most preferred is ethyl or methyl. However, $R_1$ and $R_2$ can also together be propylene, butylene or pentylene.

"Halo" or "halogen" preferably refer to F, Cl or Br. However iodine can also be employed.

"Alkenyl" is preferably vinyl, 1- or 2-propenyl, 1-butenyl, isobutenyl, sec.-butenyl. However, 1-pentenyl, iso-pentenyl or 1-hexenyl can be employed.

"Alkinyl" is preferably ethyinyl, or propyn-1-yl. However, butyn-1-, butyn-2-yl, penyn-1-, pentyn-2- or pentyn-3-yl can be employed.

The substituents $R_3$ and $R_4$ can be the same or different and are preferably, in position 3 or 4 of the phenyl ring. They are for example independently hydrogen, alkyl, alkoxy, nitro, amino, alkylamino (e.g., methylamino), dialkylamino (e.g., dimethylamino), or halo. Alternatively, $R_3$ and $R_4$ together are ethylenoxy, methylenedioxy or ethylendioxy. $R_3$ and $R_4$ also can be alkoxy (e.g., methoxy, ethoxy or propoxy).

X is preferably single or double substituted phenyl, cyclopentyl, cyclohexyl, cycloheptyl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or-4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or 4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3-, or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-,-2-,-3-,-4-,-5-,-6-,-7- or -8-quinolyl, 1,2,3,4-tetrahydro-1, -2-, -3-, -4-, -5-, -6-, -7- or -8-isoquinolyl.

The substituent(s) on the "X" ring preferably are selected from the group consisting of —COOH, —COOCH$_3$, —COOC$_2$H$_5$, —CONH$_2$, —CON(CH$_3$)$_2$, —CONHCH$_3$, —CN, —CH$_2$COOH or —CH$_2$CH$_2$COOH.

More preferred compounds useful in the practice of this invention are those in groups 1–5 below In group 1, X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH;

In group 2, $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; X is as defined in Group 1; and n is 1.

In group 3, $R_1$ and $R_2$ are as defined in group 2; $R_3$ and $R_4$ are independently selected from the group consisting of hydrogen, A, OA, halogen, —NO$_2$, —NH$_2$, —NHA or —NAA'; X is as defined in group 1; and n is 1;

In group 4, $R_1$ and $R_2$ together form a $C_{3-5}$ alkylene, $R_3$ and $R_4$ together form a moiety selected from the group consisting of —O—CH$_2$—CH$_2$—, —O, —CH$_2$—O— or —O—CH$_2$—CH$_2$—O, X is as defined in group 1; and n is 1;

Finally, in group 5, $R_1$, $R_2$ together form a $C_{3-5}$ alkylene; $R_3$ and $R_4$ are independently selected from the group consisting of hydrogen, A, OA, halogen, $NO_2$, $NH_2$, NHA or NAA'; X is as defined in group 1; and n is 1.

Processes for preparing compounds useful in this invention are described in PCT Patent Application No. 97/05530 (which is incorporated herein by reference). Those processes are set forth below. However, those processes, as well as processes for making the starting materials are reportedly known methods described in the literature (e.g., Houben-Weyl, Methods of Organic Chemistry, Georg Thieme, Stuttgart). The same reaction conditions as those known for the respective reactions can be employed.

Specifically, compounds useful in practicing this invention can be synthesized in several general ways, depending on the types of substitutions. For example, compounds of Formula I (as well as their salts) where X is a single or double substituted saturated 5–7 membered nitrogen-containing heterocycle which is connected via the nitrogen is made using a compound of Formula II

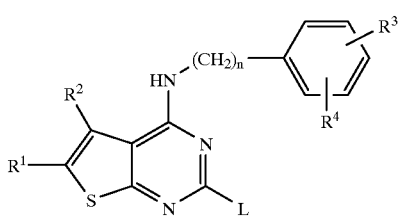

II wherein $R_1$, $R_2$, $R_3$, $R_4$ and n have the meanings above, but L is Cl, Br, OH, $SCH_3$ or a reactive esterfied OH-group. The compound of Formula II is allowed to react with a "$R_5$ substituted" saturated 5–7 membered nitrogen-containing heterocycle (where $R_5$ has the given designation).

Alternatively, the synthesis of compounds of Formula I (as well as their salts) where X is a substituted, unsaturated or saturated 5–7 membered isocycle which is connected a carbon atom on its ring to the theinopyrimidine ring is as follows. A compound of Formula III

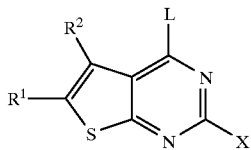

III wherein $R_1$, $R_2$ and X have the meanings described above and L is Cl, Br, OH, $SCH_3$ or a reactive esterified OH-group is allowed to react with a compound of Formula IV

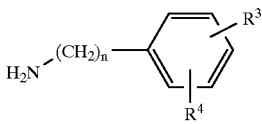

IV wherein $R_3$, $R_4$ and n have the given designations to obtain the desired compound.

In still another method to synthesize a compound of Formula I, one compound of Formula I can be converted to another. For example, a substituent $R_3$, $R_4$ and/or X can be transformed to another substituent $R_3$, $R_4$ and/or X, e.g., by the saponification of an ester, or by reduction of a nitro group. Also an acid compound of Formula I can be converted to one of its salts by treatment with a base.

If L is a reactive esterified OH-group, it is preferably alkylsulfonyloxy with $C_{1-6}$ (preferably methylsulfonyloxy) or arylsulfonyloxy with $C_{6-10}$ (preferably phenyl- or p-tolylsulfonyloxy, also 2-naphthalenesulfonyloxy).

The starting materials can also, if necessary, be made in situ so that they are not isolated from the reaction mixture but are immediately allowed to react to compounds of Formula I. On the other hand, the reaction can also be done stepwise.

The compounds of Formula I, wherein X is connected via N to the thienopyrimidine ringsystem can preferably be obtained by the reaction of compounds of formula II with unsubstituted or single or double substituted (i.e., substituted with COOH, COOA, $CONH_2$, CONAA', CONHA or CN) saturated 5–7 membered heterocyles.

The compounds of Formula II are generally known. To the extent they are not specifically known or described previously, they can be synthesized by known methods. Precursors to the compounds of Formula II can e.g., be synthesized by cyclisation or halogenation according to Med. Chem. 24, 374 (1981). Subsequent reaction with arylalkylamines yield compounds of Formula II.

In particular, the reaction of compounds of Formula II with the NH-containing heterocycle takes place in the presence or in the absence of an inert solvent at temperatures between approximately –20° C. and approximately 150° C., preferably between 20° C. and 100° C.

The addition of an acid binding agent, e.g., an alkali or alkaline earth metal hydroxide, carbonate or bicarbonate or of another salt of a weak acid of the alkali or alkaline earth metals, preferably of potassium, sodium or calcium, or the addition of an orgqanic base like triethylamine, dimethylamine, pyridine or quinoline or an excess of the amine component can be enhancing.

As inert solvents the following can be used: hydrocarbons (e.g., hexane, petrolether, benzene, toluene, xylene), chlorinated hydrocarbons (e.g., trichloroethylene, 1,2-dichlorethane, carbontetrachloride, chloroform or dichloromethane), alcohols (e.g., methanol, ethanol, isopropanol, n-propanol, n-butanol, tert. Butanol), ethers (e.g., diethylether, disopropylether, tetrahydrofurane (THF) or dioxane), glycolethers (e.g., ethyleneglycolmono methyl or monoethylether (methylglycol or ethylglycol), ethyleneglycoldimethylether (diglyme)), ketones (e.g., acetone or butanone), amides (e.g., acetamide, dimethylacetamide or dimethyl formamide (DMF)), nitriles (e.g., acetonitrile; sulfoxides like dimethysulfoxide (DMSO)), nitro compounds (e.g., nitromethane or nitrobenzene), esters (e.g., ethylacetate), or mixtures of these solvents.

Compounds of Formula III can be obtained from compounds derived from thiophenderivatives and CN-substituted heterocycles by reaction with $POCl_3$ (Eur. J. Med. Chem. 23, (1988).

The reactions of compounds of Formula III and compounds of Formula IV take place under similar conditions regarding reaction time temperature and solvent, as are described for the reactions of compounds of Formula II with NH-containing heterocycles.

To convert a substituent $R_3$ and/or $R_4$ of a compound of Formula I, to another substituent $R_3$ and/or $R_4$ e.g., by reduction of a nitrogroup (e.g., by hydration on Raney-nickel or Pd-charcoal in an inert solvent like methanol or ethanol) to an amino group or by hydrolysis of a cyano group to a carboxylic group.

An acid of formula I with a base can be converted to the corresponding addition salt e.g., by the reaction of equivalent amounts of acid and base in an inert solvent like ethanol and subsequent evaporation. For this reaction bases that yield physiologically non-toxic salts are to be used.

In this way, the acid of Formula I can be transformed with a base (e.g., sodium or potassium hydroxide or carbonate) to the corresponding metal, in particular alkali-or alkaline earth metal or the corresponding ammonium salt.

On the other hand, base of Formula I can be transformed with an acid to the corresponding acid addition salt, e.g., by reaction of equivalent amounts of base and acid in an inert solvent like ethanol and subsequent evaporation. For this reaction acids which give physiologically non-toxic salts can particularly be used, inorganic acids e.g., sulfuric acid, nitric acid, halogenhalides like hydrochloric acid or hydrobromic acid, phosphoric acids like orthophosphoric acid, sulfaminic acid; furthermore organic acids can be used, in particular aliphatic, alicyclic, araliphatic, aromatic or heterocyclic one or multiple base carbonic, sulfonic or sulfuric acids, e.g., formic acid, acetic acid, propionic acid, pivalinic acid, diethylacetic acid, malonic acid, succinic acid, pimelinic acid, fumatic acid, maleinic acid, lactic acid, tartaric acid, 2-hydroxysuccinic acid, citric acid, glucomic acid, ascorbic acid, nicotinic acid, isonicotinic acid, methan-or ethansulfonic acid, ethandisulfonic acid, 2-hydroxyethan-sulfonic acid, benzenesulfonic acid, p-toluene-sulfonic acid, naphthaline-mono- and disulfonic acids, laurylsulfric acids. Salts with physiologically not acceptable acids, e.g., picrates, can be used for the isolation and/or purification of compounds of Formula I.

In the preceding and the following all temperatures are in °C. In the following examples the "usual workup" means: if necessary, water is added, the pH is, if necessary, adjusted to values between 2 and 10, depending on the constituency of the product, extraction is done with ethylacetate or $CH_2Cl_2$, the phases are separated, the organic phase is dried over $Na_2SO_4$, evaporated and purified by chromatography on silicagel and/or crystallisation.

The foregoing may be better understood from the following examples from the aforesaid PCT patent application (which is incorporated herein by reference) that are presented for purposes illustrating compounds useful in practicing this invention and are not intended to limit the scope of the invention.

EXAMPLE 1

2-Chloro-6-Methyl-4-(3,4-Methylenedioxybenzylamino)-Thieno-[2,3-d]-Pyrimidine

A solution of 2,4-dichloro-6-methyl-thieno-[2,3-d]-pyrimidine (3.29 g) in dichloromethane (30 ml) is charged with 3,4-methylenedioxybenzylamine ("A") (3.02 g). Triethylamine (1.52 g) is added, and the mixture is stirred at room temperature. The solvent is removed, and the usual workup yields 2-chloro-6-methyl-4-(3,4-methylenedioxybenzylamino)-thieno-[2,3-d]-pyrimidine (3.38 g) Mp. 162° C.

EXAMPLE 2

2-Chloro-5-Methyl-4-(3,4-Methylenedioxybenzylamino)-Thieno-[2,3-d]-Pyrimidine

Following the procedure of Example 1, the reaction of 3,4-methylenedioxybenzylamine with 2,4-dichloro-5-methyl-thieno-[2,3-d]-pyrimidine gives 2-chloro-5-methyl-4-(3,4-methylenedioxybenzylamino)-thieno-[2,3-d]-pyrimidine

EXAMPLE 3

Following the procedure of Example 1, the reaction of 3,4-methylenedioxybenzylamine with 2,4-dichloro-5,6,7,7-tetrahydro-[1]-benzothieno-[2,3-d]-pyrimidine gives 2-chloro-5,6,7,8-tetrahydro-4-(3,4-methylenedioxybenzylamino)-[1]-benzothieno-[2,3-d]-pyrimidine Mp. 222° C.

EXAMPLE 4

Following the procedure of Example 1, the reaction of 3,4-methylenedioxybenzylamine with 2,4-dichloro-5,6-cyclopenteno-[1]-benzothieno-[2,3-d]-pyrimidine gives 2-chloro-5,6-cyclopenteno-4-(3,4-methylenedioxybenzylamino)-[1]-benzothieno-[2,3-d]-pyrimidine.

EXAMPLE 5

Following the procedure of Example 1, the reaction of 3,4-methylenedioxybenzylamine with 2,4-dichloro-5,6-cyclohepteno-[1]-benzothieno-[2,3-d]-pyrimidine gives 2-chloro-5,6-cyclohepteno-4-93,4-methylenedioxybenzylamino)-[1]-benzothieno-[2,3-d]-pyrimidine.

EXAMPLE 6

Following the procedure of Example 1, the reaction of 3,4-methylenedioxybenzylamine with 2,4-dichloro-6-ethyl-thieno-[2,3-d]-pyrimidine gives 2-chloro-6-ethyl-4-(3,4-methylenedioxybenzylamino)-thieno-[2,3-d]-pyrimidine Mp. 148° C.

EXAMPLE 7

Following the procedure of Example 1, the reaction of 3,4-methylenedioxybenzylamine with 2,4,6-trichloro-thieno-[2,3-d]-pyrimidine gives 2,6-dichloro-4-(3,4-methylenedioxybenzylamino)-thieno-[2,3-d]-pyrimidine.

EXAMPLE 8

Following the procedure of Example 1, the reaction of 3,4-methylenedioxybenzylamino with 2,4,5-trichloro-6-methyl-thieno-[2,3-d]-pyrimidine gives 2,5-dichloro-6-methyl-4-93,4-methylenedioxybenzylamino)-thieno-[2,3-d]-pyrimidine.

EXAMPLE 9

Following the procedure of Example 1, the reaction of 3,4-methylenedioxybenzylamine with 2,4-dichloro-6-nitro-thieno-[2,3-d]-pyrimidine gives 2-chloro-6-nitro-4-(3,4-methylenedioxybenzylamino)-thieno-[2,3-d]-pyrimidine.

EXAMPLE 10

Following the procedure of Example 1, the reaction of 3,4-methylenedioxybenzylamine with 2,4-dichloro-5,6-dimethyl-thieno-[2,3-d]-pyrimidine gives 2-chloro-5,6-dimethyl-4-(3,4-methylenedioxybenzylamino)-thieno-[2,3-d]-pyrimidine.

EXAMPLE 11

Following the procedure of Example 1, the reaction of 3,4-methylenedioxybenzylamine with 2,4-dichloro-6-trifluoromethyl-thieno-[2,3-d]-pyrimidine gives 2-chloro-6-trifluoromethyl-4-(3,4-methylenedioxybenzylamino)-thieno-[2,3-d]-pyrimidine.

EXAMPLE 12

Following the procedure of Example 1, the reaction of 3-chloro-4-methoxybenzylamine with 2,4-dichloro-6-methyl-thieno-[2,3-d]-pyrimidine yields 2-chloro-6-methyl-4-(3-chloro-4-methoxybenzylamino)-thieno-[2,3-d]-pyrimidine.

EXAMPLE 13

Following the procedure of Example 1, the reaction of 3-chloro-4-methoxybenzylamine with 2,4-dichloro-5-methyl-thieno-[2,3-d]-pyrimidine yields 2-chloro-5-methyl-4-(3-chloro-4-methoxybenzylamino)-thieno-[2,3-d]-pyrimidine.

EXAMPLE 14

Following the procedure of Example 1, the reaction of 3-chloro-4-methoxybenzylamine with 2,4-dichloro-5,6,7,8-tetrahydro-[1]-benzothieno-[2,3-d]-pyrimidine yields 2-chloro-5,6,7,8-tetrahydro-4-(3-chloro-4-methoxybenzylamino)-[1]-[1]-benzothieno-[2,3-d]-pyrimidine.

EXAMPLE 15

Following the procedure of Example 1, the reaction of 3-chloro4-methoxybenzylamine with 2,4-dichloro-5,6-cyclopenteno-[1]-benzothieno-[2,3-d]-pyrimidine yields 2-chloro-5,6-cyclopenteno-4-(3-chloro-4-methoybenzylamino)-[1]-benzothieno-[2,3-d]-pyrimidine.

EXAMPLE 16

Following the procedure of Example 1, the reaction of 3-chloro-4-methoxybenzylamine with 2,4-dichloro-5,6-cyclohepteno-[1]-benzothieno-[2,3-d]-pyrimidine yields 2-chloro-5,6-cyclohepteno-4-(3-chloro-4-methoxybenzylamino)-[1]-benzothieno-[2,3-d]-pyrimidine.

EXAMPLE 17

Following the procedure of Example 1, the reaction of 3-chloro-4-methoxybenzylamine with 2,4-dichloro-6-ethyl-thieno-[2,3-d]-pyrimidine yields 2-chloro-6-ethyl-4-(3-chloro-4-methoxybenzylamino)-thieno-[2,3-d]-pyrimidine.

EXAMPLE 18

Following the procedure of Example 1, the reaction of 3-chloro-4-methoxybenzylamine with 2,4,6-trichloro-thieno-[2,3-d]-pyrimidine yields 2,6-dichloro-4-93-chloro-4-methoxybenzylamino0-thieno-[2,3-d]-pyrimidine.

EXAMPLE 19

Following the procedure of Example 1, the reaction of 3-chloro-4-methoxybenzylamine with 2,4,5-trichloro-6-methyl-thieno-[2,3-d]-pyrimidine yields 2,5-dichloro-6-methyl-4-93-chloro-4-methoxybenzylamino0-thieno-[2,3-d]-pyrimidine.

EXAMPLE 20

Following the procedure of Example 1, the reaction of 3-chloro-4-methoxybenzylamine with 2,4-dichloro-6-nitro-thieno-[2,3-d]-pyrimidine yields 2-chloro-6-nitro-4-93-chloro-4-methoxybenzylamino)-thieno-[2,3-d]-pyrimidine.

EXAMPLE 21

Following the procedure of Example 1, the reaction of 3-chloro-4-methoxybenzylamine with 2,4-dichloro-5,6-dimethyl-thieno-[2,3-d]-pyrimidine yields 2-chloro-5,6-dimethyl-4-(3-chloro-4-methoxybenzylamino)-thieno-[2,3-d]-pyrimidine.

EXAMPLE 22

Following the procedure of Example 1, the reaction of 3-chloro-4-methoxybenzylamine with 2,4-dichloro-6-trifluoromethyl-thieno-[2,3-d]-pyrimidine yields 2-chloro-6-trifluoromethyl-4-(3-chloro-4-methoxybenzylamino0-thieno-[2,3-d]-pyrimidine.

EXAMPLE 23

Following the procedure of Example 1, the reaction of 3,4-dimethoxybenzylamine with 2,4-dichloro-6-methyl-thieno-[2,3-d]-pyrimidine yields 2-chloro-6-methyl-4-(3,4-dimethoxybenzylamino)-thieno-[2,3-d]-pyrimidine.

EXAMPLE 24

Following the procedure of Example 1, the reaction of 3,4-dimethoxybenzylamine with 2,4-dichloro-5-methyl-thieno-[2,3-d]-pyrimidine yields 2-chloro-5-methyl-4-(3,4-dimethoxybenzylamino0-thieno-[2,3-d]-pyrimidine.

EXAMPLE 25

Following the procedure of Example 1, the reaction of 3,4-dimethoxybenzylamine with 2,4-dichloro-5,6,7,8-tetrahydro-[1]-[1]-benzothieno-[2,3-d]-pyrimidine yields 2-chloro-5,6,7,8-tetrahydro-4-(3,4-dimethoxybenzylamino)-[1]-[1]-benzothieno-[2,3-d]-pyrimidine.

EXAMPLE 26

Following the procedure of Example 1, the reaction of 3,4-dimethoxybenzylamine with 2,4-dichloro-5,6-cyclopenteno-[1]-[1]-benzothieno-[2,3-d]-pyrimidine yields 2-chloro-5,6-cyclopenteno-4-(3,4-dimethoxybenzylamino)-[1]-benzothieno-[2,3-d]-pyrimidine.

EXAMPLE 27

Following the procedure of Example 1, the reaction of 3,4-dimethoxybenzylamine with 2,4-dichloro-5,6-cyclopenteno-[1]-benzothieno-[2,3-d]-pyrimidine yields 2-chloro-5,6-cyclopenteno-4-(3,4-dimethoxybenzylamino)-[1]-benzothieno-[2,3-d]-pyrimidine.

EXAMPLE 28

Following the procedure of Example 1, the reaction of 3,4-dimethoxybenzylamine with 2,4-dichloro-6-ethyl-thieno-[2,3-d]-pyrimidine yields 2-chloro-6-ethyl-4-(3,4-dimethoxybenzylamino)-thieno-[2,3-d]-pyrimidine.

EXAMPLE 29

Following the procedure of Example 1, the reaction of 3,4-dimethoxybenzylamine with 2,4,6-trichloro-thieno-[2,3-d]-pyrimidine yields 2,6-dichloro-4-(3,4-dimethoxybenzylamino)-thieno-[2,3-d]-pyrimidine.

EXAMPLE 30

Following the procedure of Example 1, the reaction of 3,4-dimethoxybenzylamine with 2,4,5-trichloro-6-methyl-thieno-[2,3-d]-pyrimidine yields 2,5-dichloro-6-methyl-4-(3,4-dimethoxybenzylamino)-thieno-[2,3-d]-pyrimidine.

EXAMPLE 31

Following the procedure of Example 1, the reaction of 3,4-dimethoxybenzylamine with 2,4dichloro-6-nitro-thieno-

[2,3-d]-pyrimidine yields 2-chloro-6-nitro-4-(3,4-dimethoxybenzylamino)-thieno-[2,3-d]-pyrimidine.

EXAMPLE 32

Following the procedure of Example 1, the reaction of 3,4-dimethoxybenzylamine with 2,4dichloro-5,6-dimethyl-thieno-[2,3-d]-pyrimidine yields 2-chloro-5,6-dimethyl-4-(3,4-dimethoxybenzylamino)-thieno-[2,3-d]-pyrimidine.

EXAMPLE 33

Following the procedure of Example 1, the reaction of 3,4-dimethoxybenzylamine with 2,4dichloro-6-trifluoromethyl-thieno-[2,3-d]-pyrimidine yields 2-chloro-6-trifluoromethyl-4-(3,4-dimethoxybenzylamino)-thieno-[2,3-d]-pyrimidine.

EXAMPLE 34

Following the procedure of Example 1, the reaction of benzylamine with 2,4-dichloro-6-methyl-thieno-[2,3-d]-pyrimidine yields 2-chloro-6-methyl-4-benzylamino-thieno-[2,3-d]-pyrimidine.

EXAMPLE 35

Following the procedure of Example 1, the reaction of benzylamine with 2,4-dichloro-5-methyl-thieno-[2,3-d]-pyrimidine yields 2-chloro-5-methyl-4-benzylamino-thieno-[2,3-d]-pyrimidine.

EXAMPLE 36

Following the procedure of Example 1, the reaction of benzylamine with 2,4-dichloro-5,6,7,8-tetrahydro-[1]-[1]-benzothieno-[2,3-d]-pyrimidine yields 2-chloro-5,6,7,8-tetrahydro-4-benzylamino-thieno-[1]-[1]-benzothieno-[2,3-d]-pyrimidine.

EXAMPLE 37

Following the procedure of Example 1, the reaction of benzylamine with 2,4-dichloro-5,6-cyclopenteno-[1]-benzothieno-[2,3-d]-pyrimidine yields 2-chloro-5,6-cyclopenteno-4-benzylamino-[2,3-d]-pyrimidine.

EXAMPLE 38

Following the procedure of Example 1, the reaction of benzylamine with 2,4-dichloro-5,6-cyclopenteno-[1]-benzothieno-[2,3-d]-pyrimidine yields 2-chloro-5,6-cyclopenteno-4-benzylamino-[1]-benzothieno-[2,3-d]-pyrimidine.

EXAMPLE 39

Following the procedure of Example 1, the reaction of benzylamine with 2,4-dichloro-6-ethyl-thieno-[2,3-d]-pyrimidine yields 2-chloro-6-ethyl-4-benzylamino-thieno-[2,3-d]-pyrimidine.

EXAMPLE 40

Following the procedure of Example 1, the reaction of benzylamine with 2,4,6-trichloro-thieno-[2,3-d]-pyrimidine yields 2,6-dichloro-6-4-benzylamino-thieno-[2,3-d]-pyrimidine.

EXAMPLE 41

Following the procedure of Example 1, the reaction of benzylamine with 2,4,5-trichloro-6-methyl-thieno-[2,3-d]-pyrimidine yields 2,5-dichloro-6-methyl-4-benzylamino-thieno-[2,3-d]-pyrimidine.

EXAMPLE 42

Following the procedure of Example 1, the reaction of benzylamine with 2,4-dichloro-6-nitro-thieno-[2,3-d]-pyrimidine yields 2-chloro-6-nitro-4-benzylamino-thieno-[2,3-d]-pyrimidine.

EXAMPLE 43

Following the procedure of Example 1, the reaction of benzylamine with 2,4-dichloro-5,6-dimethyl-thieno-[2,3-d]-pyrimidine yields 2-chloro-5,6-dimethyl-4-benzylamino-thieno-[2,3-d]-pyrimidine.

EXAMPLE 44

Following the procedure of Example 1, the reaction of benzylamine with 2,4-dichloro-6-trifluoromethyl-thieno-[2,3-d]-pyrimidine yields 2-chloro-6-trifluoromethyl-4-benzylamino-thieno-[2,3-d]-pyrimidine.

EXAMPLE 45

Following the procedure of Example 1, the reaction of 4-fluorobenzylamine with 2,4-dichloro-6-methyl-thieno-[2,3-d]-pyrimidine yields 2-chloro-6-methyl-4-(4-fluorobenzylamino)-thieno-[2,3-d]-pyrimidine with 2,4-dichloro-5-methyl-thieno-[2,3-d]-pyrimidine yields 2-chloro-5-methyl-4-(4-fluorobenzylamino)-thieno-[2,3-d]-pyrimidine.

EXAMPLE 46

Following the procedure of Example 1, the reaction of 4-fluorobenzylamine with 2,4-dichloro-5,6,7,8-tetrahydro-[1]-benzothieno-[2,3-d]-pyrimidine yields 2-chloro-5,6-,7,8-tetrahydro-4-(4-fluorobenzylamino)-[1]-benzothieno-[2,3-d]-pyrimidine.

EXAMPLE 47

Following the procedure of Example 1, the reaction of 4-fluorobenzylamine with 2,4-dichloro-5,6-cyclopenteno-[1]-benzothieno-[2,3-d]-pyrimidine yields 2-chloro-5,6-cyclopenteno-4-(4-fluorobenzylamino)-[1]-benzothieno-[2,3-d]-pyrimidine.

EXAMPLE 48

Following the procedure of Example 1, the reaction of 4-fluorobenzylamine with 2,4-dichloro-5,6-cyclohepteno-[1]-benzothieno-[2,3-d]-pyrimidine yields 2-chloro-5,6-cyclohepteno-4-(4-fluorobenzylamino)-[1]-benzothieno-[2,3-d]-pyrimidine.

EXAMPLE 49

Following the procedure of Example 1, the reaction of 4-fluorobenzylamine with 2,4-dichloro-6-ethyl-thieno-[2,3-d]-pyrimidine yields 2-chloro-6-ethyl-4-(4-fluorobenzylamino)-thieno-[2,3-d]-pyrimidine.

EXAMPLE 50

Following the procedure of Example 1, the reaction of 4-fluorobenzylamine with 2,4,6-trichloro-thieno-[2,3-d]-pyrimidine yields 2,6-dichloro-4-(4-fluorobenzylamino)-thieno-[2,3-d]-pyrimidine.

EXAMPLE 51

Following the procedure of Example 1, the reaction of 4-fluorobenzylamine with 2,4,5-trichloro-6-methyl-thieno-

[2,3-d]-pyrimidine yields 2,5-dichloro-6-methyl-4-(4-fluorobenzylamino)-thieno-[2,3-d]-pyrimidine.

EXAMPLE 52

Following the procedure of Example 1, the reaction of 4-fluorobenzylamine with 2,4-dichloro-6-nitro-thieno-[2,3-d]-pyrimidine yields 2-chloro-6-nitro-4-(4-fluorobenzylamino)-thieno-[2,3-d]-pyrimidine.

EXAMPLE 53

Following the procedure of Example 1, the reaction of 4-fluorobenzylamine with 2,4-dichloro-5,6-dimethyl-thieno-[2,3-d]-pyrimidine yields 2-chloro-5,6-dimethyl-4-(4-fluorobenzylamino)-thieno-[2,3-d]-pyrimidine.

EXAMPLE 54

Following the procedure of Example 1, the reaction of 4-fluorobenzylamine with 2,4-dichloro-6-trifluoromethyl-thieno-[2,3-d]-pyrimidine yields 2-chloro-6-trifluoromethyl-4-(4-fluorobenzylamino)-thieno-[2,3-d]-pyrimidine.

EXAMPLE 55

Following the procedure of Example 1, the reaction of 3,4-dichlorobenzylamine with 2,4-dichloro-6-methyl-thieno-[2,3-d]-pyrimidine yields 2-chloro-6-methyl-4-(3,4-dichlorobenzylamino)-thieno-[2,3-d]-pyrimidine.

EXAMPLE 56

Following the procedure of Example 1, the reaction of 3,4-dichlorobenzylamine with 2,4-dichloro-5-methyl-thieno-[2,3-d]-pyrimidine yields 2-chloro-5-methyl-4-(3,4-dichlorobenzylamino)-thieno-[2,3-d]-pyrimidine.

EXAMPLE 57

Following the procedure of Example 1, the reaction of 3,4-dichlorobenzylamine with 2,4-dichloro-5,6,7,8-tetrahydro-[1]-benzothieno-[2,3-d]-pyrimidine yields 2-chloro-5,6,7,8-tetrahydro-4-(3,4-dichlorobenzylamino)-[1]-benzothieno-[2,3-d]-pyrimidine.

EXAMPLE 58

Following the procedure of Example 1, the reaction of 3,4-dichlorobenzylamine with 2,4-dichloro-5,6-cyclopenteno-[1]-benzothieno-[2,3-d]-pyrimidine yields 2-chloro-5,6-cyclopenteno-4-(3,4-dichlorobenzylamino)-[1]-benzothieno-[2,3-d]-pyrimidine.

EXAMPLE 59

Following the procedure of Example 1, the reaction of 3,4-dichlorobenzylamine with 2,4-dichloro-5,6-cyclopenteno-[1]-benzothieno-[2,3-d]-pyrimidine yields 2-chloro-5,6-cyclopenteno-4-(3,4-dichlorobenzylamino)-[1]-benzothieno-[2,3-d]-pyrimidine.

EXAMPLE 60

Following the procedure of Example 1, the reaction of 3,4-dichlorobenzylamine with 2,4-dichloro-6-ethyl-thieno-[2,3-d]-pyrimidine yields 2-chloro-6-ethyl-4-(3,4-dichlorobenzylamino)-thieno-[2,3-d]-pyrimidine.

EXAMPLE 61

Following the procedure of Example 1, the reaction of 3,4-dichlorobenzylamine with 2,4,6-trichloro-thieno-[2,3-d]-pyrimidine yields 2-6-dichloro-4-(3,4-dichlorobenzylamino)-thieno-[2,3-d]-pyrimidine.

EXAMPLE 62

Following the procedure of Example 1, the reaction of 3,4-dichlorobenzylamine with 2,4,5-trichloro-6-methyl-thieno-[2,3-d]-pyrimidine yields 2,5-dichloro-6-methyl-4-(3,4-dichlorobenzylamino)-thieno-[2,3-d]-pyrimidine.

EXAMPLE 63

Following the procedure of Example 1, the reaction of 3,4-dichlorobenzylamine with 2,4-dichloro-6-nitro-thieno-[2,3-d]-pyrimidine yields 2-chloro-6-nitro-4-(3,4-dichlorobenzylamino)-thieno-[2,3-d]-pyrimidine.

EXAMPLE 64

Following the procedure of Example 1, the reaction of 3,4-dichlorobenzylamine with 2,4-dichloro-5,6-dimethyl-thieno-[2,3-d]-pyrimidine yields 2-chloro-5,6-dimethyl-4-(3,4-dichlorobenzylamino)-thieno-[2,3-d]-pyrimidine.

EXAMPLE 65

Following the procedure of Example 1, the reaction of 3,4-dichlorobenzylamine with 2,4-dichloro-6-trifluoromethyl-thieno-[2,3-d]-pyrimidine yields 2-chloro-6-trifluoromethyl-4-(3,4-dichlorobenzylamino)-thieno-[2,3-d]-pyrimidine.

EXAMPLE 66

Following the procedure of Example 1, the reaction of 3-nitrobenzylamine with 2,4-dichloro-6-methyl-thieno-[2,3-d]-pyrimidine yields 2-chloro-6-methyl-4-(3-nitrobenzylamino)-thieno-[2,3-d]-pyrimidine.

EXAMPLE 67

Following the procedure of Example 1, the reaction of 3-nitrobenzylamine with 2,4-dichloro-5-methyl-thieno-[2,3-d]-pyrimidine yields 2-chloro-5-methyl-4-(3-nitrobenzylamino)-thieno-[2,3-d]-pyrimidine.

EXAMPLE 68

Following the procedure of Example 1, the reaction of 3-nitrobenzylamine with 2,4-dichloro-5,6,7,8-tetrahydro-[1]-benzothieno-[2,3-d]-pyrimidine yields 2-chloro-5,6,7,8-tetrahydro-4-(3-nitrobenzylamino)-[1]-benzothieno-[2,3-d]-pyrimidine.

EXAMPLE 69

Following the procedure of Example 1, the reaction of 3-nitrobenzylamine with 2,4-dichloro-5,6-cyclopenteno-[1]-benzothieno-[2,3-d]-pyrimidine yields 2-chloro-5,6-cyclopenteno-4-(3-nitrobenzylamino)-[1]-benzothieno-[2,3-d]-pyrimidine.

EXAMPLE 70

Following the procedure of Example 1, the reaction of 3-nitrobenzylamine with 2,4-dichloro-5,6-cyclopenteno-[1]-benzothieno-[2,3-d]-pyrimidine yields 2-chloro-5,6-cyclopenteno-4-(3-nitrobenzylamino)-[1]-benzothieno-[2,3-d]-pyrimidine.

EXAMPLE 71

Following the procedure of Example 1, the reaction of 3-nitrobenzylamine with 2,4-dichloro-6-ethyl-thieno-[2,3- d]-pyrimidine yields 2-chloro-6-ethyl-4-(3-nitrobenzylamino)-thieno-[2,3-d]-pyrimidine.

EXAMPLE 72

Following the procedure of Example 1, the reaction of 3-nitrobenzylamine with 2,4,6-trichloro-thieno-[2,3-d]-pyrimidine yields 2,6-dichloro-4-(3-nitrobenzylamino)-thieno-[2,3-d]-pyrimidine.

EXAMPLE 73

Following the procedure of Example 1, the reaction of 3-nitrobenzylamine with 2,4,5-trichloro-6-methyl-thieno-[2,3-d]-pyrimidine yields 2,5-dichloro-6-methyl-4-(3-nitrobenzylamino)-thieno-[2,3-d]-pyrimidine.

EXAMPLE 74

Following the procedure of Example 1, the reaction of 3-nitrobenzylamine with 2,4-dichloro-6-nitro-thieno-[2,3-d]-pyrimidine yields 2-chloro-6-nitro-4-(3-nitrobenzylamino)-thieno-[2,3-d]-pyrimidine.

EXAMPLE 75

Following the procedure of Example 1, the reaction of 3-nitrobenzylamine with 2,4-dichloro-5,6-dimethyl-thieno-[2,3-d]-pyrimidine yields 2-chloro-5,6-dimethyl-4-(3-nitrobenzylamino)-thieno-[2,3-d]-pyrimidine.

EXAMPLE 76

Following the procedure of Example 1, the reaction of 3-nitrobenzylamine with 2,4-dichloro-6-trifluoromethyl-thieno-[2,3-d]-pyrimidine yields 2-chloro-6-trifluoromethyl-4-(3-nitrobenzylamino)-thieno-[2,3-d]-pyrimidine.

EXAMPLE 77

Following the procedure of Example 1, the reaction of 3,4-methylenedioxyphenethylamine with 2,4-dichloro-6-methyl-thieno-[2,3-d]-pyrimidine yields 2-chloro-6-methyl-4-(3-nitrobenzylamino)-thieno-[2,3-d]-pyrimidine.

EXAMPLE 78

Following the procedure of Example 1, the reaction of 3,4-methylenedioxyphenethylamine with 2,4-dichloro-5-methyl-thieno-[2,3-d]-pyrimidine yields 2-chloro-5-methyl-4-(3,4-methylenedioxyphenethylamino)-thieno-[2,3-d]-pyrimidine.

EXAMPLE 79

Following the procedure of Example 1, the reaction of 3,4-methylenedioxyphenethylamine with 2,4-dichloro-5,6,7,8-tetrahydro-[1]-benzothieno-[2,3-d]-pyrimidine yields 2-chloro-5,6,7,8-tetrahydro-4-(3,4-methylenedioxyphenethylamino)-[1]-benzothieno-[2,3-d]-pyrimidine.

EXAMPLE 80

Following the procedure of Example 1, the reaction of 3,4-methylenedioxyphenethylamine with 2,4-dichloro-5,6-cyclopenteno-[1]-benzothieno-[2,3-d]-pyrimidine yields 2-chloro-5,6-cyclopenteno-4-(3,4-methylenedioxyphenethylamino)-[1]-benzothieno-[2,3-d]-pyrimidine.

EXAMPLE 81

Following the procedure of Example 1, the reaction of 3,4-methylenedioxyphenethylamine with 2,4-dichloro-6-ethyl-thieno-[2,3-d]-pyrimidine yields 2-chloro-6-ethyl-4-(3,4-methylenedioxyphenethylamino)-thieno-[2,3-d]-pyrimidine.

EXAMPLE 82

Following the procedure of Example 1, the reaction of 3,4-methylenedioxyphenethylamine with 2,4,6-trichloro-thieno-[2,3-d]-pyrimidine yields 2,6-dichloro-4-(3,4-methylenedioxyphenethylamino)-thieno-[2,3-d]-pyrimidine.

EXAMPLE 83

Following the procedure of Example 1, the reaction of 3,4-methylenedioxyphenethylamine with 2,4,5-trichloro-6-methyl-thieno-[2,3-d]-pyrimidine yields 2,5-dichloro-6-methyl-4-(3,4-methylenedioxyphenethylamino)-thieno-[2,3-d]-pyrimidine.

EXAMPLE 84

Following the procedure of Example 1, the reaction of 3,4-methylenedioxyphenethylamine with 2,4-dichloro-6-nitro-thieno-[2,3-d]-pyrimidine yields 2-chloro-6-nitro-4-(3,4-methylenedioxyphenethylamino)-thieno-[2,3-d]-pyrimidine.

EXAMPLE 85

Following the procedure of Example 1, the reaction of 3,4-methylenedioxyphenethylamine with 2,4-dichloro-5,6-dimethyl-thieno-[2,3-d]-pyrimidine yields 2-chloro-5,6-dimethyl-4-(3,4-methylenedioxyphenethylamino)-thieno-[2,3-d]-pyrimidine.

EXAMPLE 86

Following the procedure of Example 1, the reaction of 3,4-methylenedioxyphenethylamine with 2,4-dichloro-6-trifluoromethyl-thieno-[2,3-d]-pyrimidine yields 2-chloro-6-trifluoromethyl-4-(3,4-methylenedioxyphenethylamino)-thieno-[2,3-d]-pyrimidine.

EXAMPLE 87

Following the procedure of Example 1, the reaction of 3,4-ethylendioxyphenethylamine with 2,4-dichloro-6-methyl-thieno-[2,3-d]-pyrimidine yields 2-chloro-6-methyl-4-(3,4-ethylendioxybenzylamino)-thieno-[2,3-d]-pyrimidine.

EXAMPLE 88

Following the procedure of Example 1, the reaction of 3,4-ethylendioxyphenethylamine with 2,4-dichloro-5-methyl-thieno-[2,3-d]-pyrimidine yields 2-chloro-5-methyl-4-(3,4-ethylendioxybenzylamino)-thieno-[2,3-d]-pyrimidine.

EXAMPLE 89

Following the procedure of Example 1, the reaction of 3,4-ethylendioxyphenethylamine with 2,4-dichloro-5,6,7,8-tetrahydro-[1]-benzothieno-[2,3-d]-pyrimidine yields 2-chloro-5,6,7,8-tetrahydro-4-(3,4-ethylendioxybenzylamino)-[1]-benzothieno-[2,3-d]-pyrimidine.

EXAMPLE 90

Following the procedure of Example 1, the reaction of 3,4-ethylendioxyphenethylamine with 2,4-dichloro-6-ethylthieno-[2,3-d]-pyrimidine yields 2-chloro-6-ethyl-4-(3,4-ethylendioxybenzylamino)-thieno-[2,3-d]-pyrimidine.

EXAMPLE 91

Following the procedure of Example 1, the reaction of 3,4-ethylendioxyphenethylamine with 2,4,6-trichloro-thieno-[2,3-d]-pyrimidine yields 2,6-dichloro-4-(3,4-ethylendioxybenzylamino)-thieno-[2,3-d]-pyrimidine.

EXAMPLE 92

Following the procedure of Example 1, the reaction of 3,4-ethylendioxyphenethylamine with 2,4,5-trichloro-6-methyl-thieno-[2,3-d]-pyrimidine yields 2,5-dichloro-6-methyl-4-(3,4-ethylendioxybenzylamino)-thieno-[2,3-d]-pyrimidine.

EXAMPLE 93

Following the procedure of Example 1, the reaction of 3,4-ethylendioxyphenethylamine with 2,4-dichloro-6-nitro-thieno-[2,3-d]-pyrimidine yields 2-chloro-6-nitro-4-(3,4-ethylendioxybenzylamino)-thieno-[2,3-d]-pyrimidine.

EXAMPLE 94

Following the procedure of Example 1, the reaction of 3,4-ethylendioxyphenethylamine with 2,4-dichloro-5,6-dimethyl-thieno-[2,3-d]-pyrimidine yields 2-chloro-5,6-dimethyl-4-(3,4-ethylendioxybenzylamino)-thieno-[2,3-d]-pyrimidine.

EXAMPLE 95

Following the procedure of Example 1, the reaction of 3,4-ethylendioxyphenethylamine with 2,4-dichloro-6-trimethyl-thieno-[2,3-d]-pyrimidine yields 2-chloro-6-trifluoromethyl-4-(3,4-ethylendioxybenzylamino)-thieno-[2,3-d]-pyrimidine.

EXAMPLE 96

2-Chloro-6-methyl-4-(3,4-methylenedioxybenzylamino)-thieno-[2,3-d]-pyrimidine (1.67 g) and piperidine-4-carboxylic acid ethylester (3 g) are heated to 130° C. After cooling, the residue is dissolved in dichloromethane. The usual workup yields 1-[6-methyl-4-(3,4-methyleneedioxybenzylamino)-thieno-[2,3-d]-2-yl]-piperidine-4-carboxylic acid ethylester (0.5 g).

EXAMPLES 97–195

Following the procedure of Example 96, the reaction of a piperdine-4-carboxylic acid ethylester with the appropriate 2-chloro-thieno-[2,3-d]-pyrimidine-derivative having an arylalkylamine substituent in position 4 (included among Examples 1–95), the following compounds are obtained:

1-5-methyl-4-(3,4-methylenedioxybenzylamino)-thieno-[2,3-d]-pyrimidin-2-yl]-piperidinyl-4-carboxylic acid ethylester (Example 97);

1-[5,6,7,8-tetrahydro-4-)3,4-methylenedioxybenzylamino)-[1]-benzothieno-[2,3-d]-pyrimidin-2-yl]-piperidinyl-4-carboxylic acid ethylester (Example 98);

1-[5,6-cyclopenteno-4-(3,4-methylenedioxybenzylamino)-[1]-benzothieno-[2,3-d]-pyrimidine-2-yl]-piperidine-4-carboxylic acid ethylester (Example 99);

1-[5,6-cyclohepteno-4-(3,4-methylenedioxybenzylamino)-[1]-benzothieno-[2,3-d]-pyrimidine-2-yl]-piperidine-4-carboxylic acid ethylester (Example 100);

1-[6-ethyl-4-(3,4-methylenedioxybenzylamino)-thieno-[2,3-d]-pyrimidine-2-yl]-piperidine-4-carboxylic acid ethylester (Example 101);

1-[6-chloro-4-(3,4-methylenedioxybenzylamino)-thieno-[2,3-d]-pyrimidine-2-yl]-piperidine-4-carboxylic acid ethylester (Example 102);

1-[5-chloro-6-methyl-4-(3,4-methylenedioxybenzylamino)-thieno-[2,3-d]-pyrimidine-2-yl]-piperidine-4-carboxylic acid ethylester (Example 103);

1-[6-nitro-4-(3,4-methylenedioxybenzylamino)-thieno-[2,3-d]-pyrimidine-2-yl]-piperidine-4-carboxylic acid ethylester (Example 104);

1-[5,6-dimethyl-4-(3,4-methylenedioxybenzylamino)-thieno-[2,3-d]-pyrimidine-2-yl]-piperidine-4-carboxylic acid ethylester (Example 105);

1-[6-trifluoromethyl-4-(3,4-methylenedioxybenzylamino)-thieno-[2,3-d]-pyrimidine-2-yl]-piperidine-4-carboxylic acid ethylester (Example 106);

1-[6-methyl-4-(3-chloro-4-methoxybenzylamino)-thieno-[2,3-d]-pyrimidine-2-yl]-piperidine-4-carboxylic acid ethylester (Example 107);

1-[5-methyl-4-(3-chloro-4-methoxybenzylamino)-thieno-[2,3-d]-pyrimidine-2-yl]-piperidine-4-carboxylic acid ethylester (Example 108);

1-[5,6,7,8-tetrahydro-4-(3-chloro-4-methoxybenzylamino)-[1]-benzothieno-[2,3-d]-pyrimidin-2-yl]-piperidinyl-4-carboxylic acid ethylester (Example 109);

1-[5,6-cyclopenteno-4-(3-chloro-4-methoxybenzylamino)-[1]-benzothieno-[2,3-d]-pyrimidin-2-yl-piperidinyl-4-carboxylic acid ethylester (Example 110);

1-[5,6-cyclohepteno-4-(3-chloro-4-methoxybenzylamino)-[1]-benzothieno-[2,3-d]-pyrimidin-2-yl]-piperidinyl-4-carboxylic acid ethylester (Example 111);

1-[6-ethyl-4-(3-chloro-4-methoxybenzylamino)-thieno-[2,3-d]-pyrimidin-2-yl]-piperidinyl-4-carboxylic acid ethylester (Example 112);

1-[6-chloro-4-(3-chloro-4-methoxybenzylamino)-thieno-[2,3-d]-pyrimidin-2-yl]-piperidinyl-4-carboxylic acid ethylester (Example 113);

1-[5-chloro-6-methyl-4-(3-chloro-4-methoxybenzylamino)-thieno-[2,3-d]-pyrimidin-2-yl]-piperidinyl-4-carboxylic acid ethylester (Example 114);

1-[6-nitro-4-(3-chloro-4-methoxybenzylamino)-thieno-[2,3-d]-pyrimidin-2-yl]-piperidinyl-4-carboxylic acid ethylester (Example 115);

1-[5,6-dimethyl-4-(3-chloro-4-methoxybenzylamino)-thieno-[2,3 -d]-pyrimidin-2-yl]-piperidinyl-4-carboxylic acid ethylester (Example 116);

1-[6-trifluoromethyl-4-(3-chloro-4-methoxybenzylamino)-thieno-[2,3-d]-pyrimidin-2-yl]-piperidinyl-4-carboxylic acid ethylester (Example 117);

1-[6-methyl-4-(3,4-dimethoxybenzylamino)-thieno-[2,3-d]-pyrimidin-2-yl]-piperidinyl-4-carboxylic acid ethylester (Example 118);

1-[5-methyl-4-(3,4-dimethoxybenzylamino)-thieno-[2,3-d]-pyrimidin-2-yl]-piperidinyl-4-carboxylic acid ethylester (Example 119);

1-[5,6,7,8-tetrahydro-4-(3,4-dimethoxybenzylamino)-[1]-benzothieno-[2,3-d]-pyrimidin-2-yl]-piperidinyl-4-carboxylic acid ethylester (Example 120);

1-[5,6-cyclopenteno-4-(3,4-dimethoxybenzylamino)-[1]-benzothieno-[2,3-d]-pyrimidin-2-yl]-piperidinyl-4-carboxylic acid ethylester (Example 121);

1-[5,6-cyclohepteno-4-(3,4-dimethoxybenzylamino)-[1]-benzothieno-[2,3-d]-pyrimidin-2-yl]-piperidinyl-4-carboxylic acid ethylester (Example 122);

1-[6-ethyl-4-(3,4-dimethoxybenzylamino)-thieno-[2,3-d]-pyrimidin-2-yl]-piperidinyl-4-carboxylic acid ethylester (Example 123);

1-[6-chloro-4-(3,4-dimethoxybenzylamino)-thieno-[2,3-d]-pyrimidin-2-yl]-piperidinyl-4-carboxylic acid ethylester (Example 124);

1-[5-chloro-6-methyl-4-(3,4-dimethoxybenzylamino)-thieno-[2,3-d]-pyrimidin-2-yl]-piperidinyl-4-carboxylic acid ethylester (Example 125);

1-[6-nitro-4-(3,4-dimethoxybenzylamino)-thieno-[2,3-d]-pyrimidin-2-yl]-piperidinyl-4-carboxylic acid ethylester (Example 126);

1-[5,6-dimethyl-4-(3,4-dimethoxybenzylamino)-thieno-[2,3-d]-pyrimidin-2-yl]-piperidinyl-4-carboxylic acid ethylester (Example 127);

1-[6-trifluoromethyl-4-(3,4-dimethoxybenzylamino)-thieno-[2,3-d]-pyrimidin-2-yl]-piperidinyl-4-carboxylic acid ethylester (Example 128);

1-[6-methyl-4-(3,4-dimethoxybenzylamino)-thieno-[2,3-d]-pyrimidin-2-yl]-piperidinyl-4-carboxylic acid ethylester (Example 129);

1-(6-methyl-4-benzylamino-thieno-[2,3-d]-pyrimidin-2-yl)-piperidinyl-4-carboxylic acid ethylester (Example 130);

1-(5-methyl-4-benzylamino-thieno-[2,3-d]-pyrimidin-2-yl)-piperidinyl-4-carboxylic acid ethylester (Example 131);

1-(5,6,7,8-tetrahydro-4-benzylamino-[1]-benzothieno-[2,3-d]-pyrimidin-2-yl)-piperidinyl-4-carboxylic acid ethylester (Example 132);

1-(5,6-cyclopenteno-4-benzylamino-[1]-benzothieno-[2,3-d]-pyrimidin-2-yl)-piperidinyl-4-carboxylic acid ethylester (Example 133);

1-(5,6-cyclohepteno-4-benzylamino-[1]-benzothieno-[2,3-d]-pyrimidin-2-yl)-piperidinyl-4-carboxylic acid ethylester (Example 134);

1-(6-ethyl-4-benzylamino-thieno-[2,3-d]-pyrimidin-2-yl)-piperidinyl-4-carboxylic acid ethylester (Example 135);

1-(6-chloro-4-benzylamino-thieno-[2,3-d]-pyrimidin-2-yl]-piperidinyl-4-carboxylic acid ethylester (Example 136);

1-(5-chloro-6-methyl-4-benzylamino-thieno-[2,3-d]-pyrimidin-2-yl)-piperidinyl-4-carboxylic acid ethylester (Example 137);

1-(6-nitro-4-benzylamino-thieno-[2,3-d]-pyrimidin-2-yl]-piperidinyl-4-carboxylic acid ethylester (Example 138);

1-(5,6-dimethyl-4-benzylamino-thieno-[2,3-d]-pyrimidin-2-yl)-piperidinyl-4-carboxylic acid ethylester (Example 139);

1-(6-trifluoromethyl-4-benzylamino-thieno-[2,3-d]-pyrimidin-2-yl)-piperidinyl-4-carboxylic acid ethylester (Example 140);

1-[6-methyl-4-(4-fluorobenzylamino)-thieno-[2,3-d]-pyrimidin-2-yl]-piperidinyl-4-carboxylic acid ethylester (Example 141);

1-[5-methyl-4-(4-fluorobenzylamino)-thieno-[2,3-d]-pyrimidin-2-yl]-piperidinyl-4-carboxylic acid ethylester (Example 142);

1-[5,6,7,8-tetrahydro-4-(4-fluorobenzylamino)-[1]-benzothieno-[2,3-d]-pyrimidin-2-yl]-piperidinyl-4-carboxylic acid ethylester (Example 143);

1-[5,6-cyclopenteno-4-(4-fluorobenzylamino)-[1]-benzothieno-[2,3-d]-pyrimidin-2-yl]-piperidinyl-4-carboxylic acid ethylester (Example 144);

1-[5,6-cyclohepteno-4-(4-fluorobenzylamino)-[1]-benzothieno-[2,3-d]-pyrimidin-2-yl]-piperidinyl-4-carboxylic acid ethylester (Example 145);

1-[6-ethyl-4-(4-fluorobenzylamino)-thieno-[2,3-d]-pyrimidin-2-yl-piperidinyl-4- carboxylic acid ethylester (Example 146);

1-[6-chloro-4-(4-fluorobenzylamino)-thieno-[2,3-d]-pyrimidin-2-yl-piperidinyl-4-carboxylic acid ethylester (Example 147);

1-[5-chloro-6-methyl-4-(4-fluorobenzylamino)-thieno-[2,3-d]-pyrimidin-2-yl]-piperidinyl-4-carboxylic acid ethylester (Example 148);

1-[6-nitro-4-(4-fluorobenzylamino)-thieno-[2,3-d]-pyrimidin-2-yl-piperidinyl-4-carboxylic acid ethylester (Example 149);

1-[5,6-dimethyl-4-(4-fluorobenzylamino)-thieno-[2,3-d]-pyrimidin-2-yl]-piperidinyl-4-carboxylic acid ethylester (Example 150);

1-[6-trifluoromethyl-4-(4-fluorobenzylamino)-thieno-[2,3-d]-pyrimidin-2-yl]-piperidinyl-4-carboxylic acid ethylester (Example 151);

1-[6-methyl-4-(3,4-dichlorobenzylamino)-thieno-[2,3-d]-pyrimidin-2-yl]-piperidinyl-4-carboxylic acid ethylester (Example 152);

1-[5-methyl-4-(3,4-dichlorobenzylamino)-thieno-[2,3-d]-pyrimidin-2-yl]-piperidinyl-4-carboxylic acid ethylester (Example 153);

1-[5,6,7,8-tetrahydro-4-(3,4-dichlorobenzylamino)-[1]-benzothieno-[2,3-d]-pyrimidin-2-yl]-piperidinyl-4-carboxylic acid ethylester (Example 154);

1-[5,6-cyclopenteno-4-(3,4-dichlorobenzylamino)-[1]-benzothieno-[2,3-d]-pyrimidin-2-yl]-piperidinyl-4-carboxylic acid ethylester (Example 155);

1-[5,6-cyclohepteno-4-(3,4-dichlorobenzylamino)-[1]-benzothieno-[2,3-d]-pyrimidin-2-yl]-piperidinyl-4-carboxylic acid ethylester (Example 156);

1-[6-ethyl-4-(3,4-dichlorobenzylamino)-thieno-[2,3-d]-pyrimidin-2-yl]-piperidinyl-4-carboxylic acid ethylester (Example 157);

1-[6-chloro-4-(3,4-dichlorobenzylamino)-thieno-[2,3-d]-pyrimidin-2-yl]-piperidinyl-4-carboxylic acid ethylester (Example 158);

1-[5-chloro-6-methyl-4-(3,4-dichlorobenzylamino)-thieno-[2,3-d]-pyrimidin-2-yl]-piperidinyl-4-carboxylic acid ethylester (Example 159);

1-[6-nitro-4-(3,4-dichlorobenzylamino)-thieno-[2,3-d]-pyrimidin-2-yl]-piperidinyl-4-carboxylic acid ethylester (Example 160);

1-[5,6-dimethyl-4-(3,4-dichlorobenzylamino)-thieno-[2,3-d]-pyrimidin-2-yl]-piperidinyl-4-carboxylic acid ethylester (Example 161);

1-[6-trifluoromethyl-4-(3,4-dichlorobenzylamino)-thieno-[2,3-d]-pyrimidin-2-yl]-piperidinyl-4-carboxylic acid ethylester (Example 162);

1-[6-methyl-4-(3-nitrobenzylamino)-thieno-[2,3-d]-pyrimidin-2-yl]-piperidinyl-4-carboxylic acid ethylester (Example 163);

1-[5-methyl-4-(3-nitrobenzylamino)-thieno-[2,3-d]-pyrimidin-2-yl]-piperidinyl-4-carboxylic acid ethylester (Example 164);

1-[5,6,7,8-tetrahydro-4-(3-nitrobenzylamino)-[1]-benzothieno-[2,3-d]-pyrimidin-2-yl]-piperidinyl-4-carboxylic acid ethylester (Example 165);

1-[5,6-cyclopenteno-4-(3-nitrobenzylamino)-[1]-benzothieno-[2,3-d]-pyrimidin-2-yl]-piperidinyl-4-carboxylic acid ethylester (Example 166);

1-[5,6-cyclohepteno-4-(3-nitrobenzylamino)-[1]-benzothieno-[2,3-d]-pyrimidin-2-yl]-piperidinyl-4-carboxylic acid ethylester (Example 167);

1-[6-ethyl-4-(3-nitrobenzylamino)-thieno-[2,3-d]-pyrimidin-2-yl]-piperidinyl-4-carboxylic acid ethylester (Example 168);

1-[6-chloro-4-(3-nitrobenzylamino)-thieno-[2,3-d]-pyrimidin-2-yl]-piperidinyl-4-carboxylic acid ethylester (Example 169);

1-[5-chloro-6-methyl-4-(3-nitrobenzylamino)-thieno-[2,3-d]-pyrimidin-2-yl]-piperidinyl-4-carboxylic acid ethylester (Example 170);

1-[6-nitro-4-(3-nitrobenzylamino)-thieno-[2,3-d]-pyrimidin-2-yl]-piperidinyl-4-carboxylic acid ethylester (Example 171);

1-[5,6-dimethyl-4-(3-nitrobenzylamino)-thieno-[2,3-d]-pyrimidin-2-yl]-piperidinyl-4-carboxylic acid ethylester (Example 172);

1-[6-trifluoromethyl-4-(3-nitrobenzylamino)-thieno-[2,3-d]-pyrimidin-2-yl]-piperidinyl-4-carboxylic acid ethylester (Example 173);

1-[6-methyl-4-(3,4-methylenedioxyphenethylamino)-thieno-[2,3-d]-pyrimidin-2-yl]-piperidinyl-4-carboxylic acid ethylester (Example 174);

1-[5-methyl-4-(3,4-methylenedioxyphenethylamino)-thieno-[2,3-d]-pyrimidin-2-yl]-piperidinyl-4-carboxylic acid ethylester (Example 175);

1-[5,6,7,8-tetrahydro-4-(3,4-methylenedioxyphenethylamino)-[1]-benzothieno-[2,3-d]-pyrimidin-2-yl]-piperidinyl-4-carboxylic acid ethylester (Example 176);

1-[5,6-cyclopenteno-4-(3,4-methylenedioxyphenethylamino)-[1]-benzothieno-[2,3-d]-pyrimidin-2-yl]-piperidinyl-4-carboxylic acid ethylester (Example 177);

1-[5,6-cyclohepteno-4-(3,4-methylenedioxyphenethylamino)-[1]-benzothieno-[2,3-d]-pyrimidin-2-yl]-piperidinyl-4-carboxylic acid ethylester (Example 178);

1-[6-ethyl-4-(3,4-methylenedioxyphenethylamino)-thieno-[2,3-d]-pyrimidin-2-yl]-piperidinyl-4-carboxylic acid ethylester (Example 179);

1-[6-chloro-4-(3,4-methylenedioxyphenethylamino)-thieno-[2,3-d]-pyrimidin-2-yl]-piperidinyl-4-carboxylic acid ethylester (Example 180);

1-[5-chloro-6-methyl-4-(3,4-methylenedioxyphenethylamino)-thieno-[2,3-d]-pyrimidin-2-yl]-piperidinyl-4-carboxylic acid ethylester (Example 181);

1-[6-nitro-4-(3,4-methylenedioxyphenethylamino)-thieno-[2,3-d]-pyrimidin-2-yl]-piperidinyl-4-carboxylic acid ethylester (Example 182);

1-[5,6-dimethyl-4-(3,4-methylenedioxyphenethylamino)-thieno-2,3-d]-pyrimidin-2-yl]-piperidinyl-4-carboxylic acid ethylester (Example 183);

1-[6-trifluoromethyl-4-(3,4-methylenedioxyphenethylamino)-thieno-[2,3-d]-pyrimidin-2-yl]-piperidinyl-4-carboxylic acid ethylester (Example 184);

1-[6-methyl-4-(3,4-ethylendioxybenzylamino)-thieno-[2,3-d]-pyrimidin-2-yl]-piperidinyl-4-carboxylic acid ethylester (Example 185);

1-[5-methyl-4-(3,4-ethylendioxybenzylamino)-thieno-[2,3-d]-pyrimidin-2-yl]-piperidinyl-4-carboxylic acid ethylester (Example 186);

1-[5,6,7,8-tetrahydro-4-(3,4-ethylendioxybenzylamino)-[1]-benzothieno-[2,3-d]-pyrimidin-2-yl]-piperidinyl-4-carboxylic acid ethylester (Example 187);

1-[5,6-cyclopenteno-4-(3,4-ethylendioxybenzylamino)-[1]-benzothieno-[2,3-d]-pyrimidin-2-yl]-piperidinyl-4-carboxylic acid ethylester (Example 188);

1-[5,6-cyclohepteno-4-(3,4-ethylendioxybenzylamino)-[1]-benzothieno-[2,3-d]-pyrimidin-2-yl]-piperidinyl-4-carboxylic acid ethylester (Example 189);

1-[6-ethyl-4-(3,4-ethylendioxybenzylamino)-thieno-[2,3-d]-pyrimidin-2-yl]-piperidinyl-4-carboxylic acid ethylester (Example 190);

1-[6-chloro-4-(3,4-ethylendioxybenzylamino)-thieno-[2,3-d]-pyrimidin-2-yl]-piperidinyl-4-carboxylic acid ethylester (Example 191);

1-[5-chloro-6-methyl-4-(3,4-ethylendioxybenzylamino)-thieno-[2,3-d]-pyrimidin-2-yl]-piperidinyl-4-carboxylic acid ethylester (Example 192);

1-[6-nitro-4-(3,4-ethylendioxybenzylamino)-thieno-[2,3-d]-pyrimidin-2-yl]-piperidinyl-4-carboxylic acid ethylester (Example 193);

1-[5,6-dimethyl-4-(3,4-ethylendioxybenzylamino)-thieno-[2,3-d]-pyrimidin-2-yl]-piperidinyl-4-carboxylic acid ethylester (Example 194);

1-[6-trifluoromethyl-4-(3,4-ethylendioxybenzylamino)-thieno-[2,3-d]-pyrimidin-2-yl]-piperidinyl-4-carboxylic acid ethylester (Example 195);

EXAMPLE 196

Sodium Salt of 1-[6-Methyl-4-(3,4-Methylenedioxy-Benzylamino)-Thieno-[2,3-d]-Pyrimidin-2-yl]-Piperidinyl-4-Carboxylic Acid 1-[6-Methyl-4-(3,4-methylenedioxybenzylamino)-thieno-[2,3-d]-pyrimidin-2-yl]-piperidinyl-4-carboxylic acid ethylester (0.5 g) in methanol (70 ml) is charged with 2N NaOH (30 ml), and is stirred 4 hours at 50° C. The solvent is removed, and the residue is washed with cold water to yield the sodium salt of 1-[6-methyl-4-(3,4-methylenedioxy-benzylamino)-thieno-[2,3-d]-pyrimidin-2-yl]-piperidinyl-4-carboxylic acid (1.5 g) m.p. 272° C.

EXAMPLES 197–295

Following the procedure of Example 196, the following carboxylic acids can be obtained from the esters from Examples 97–195.

1-[5-methyl-4-(3,4-methylenedioxybenzylamino)-thieno-[2,3-d]-pyrimidin-2-yl]-piperidinyl-4-carboxylic acid (Example 197);

1-[5,6,7,8-tetrahydro-4-(3,4-methylenedioxybenzylamino)-[1]-benzothieno-[2,3-d]-pyrimidin-2-yl]-piperidinyl-4-carboxylic acid, monohydrate amorphous (Example 198);

1-[5,6-cyclopenteno-4-(3,4-methylenedioxybenzylamino)-[1]-benzothieno-[2,3-d]-pyrimidin-2-yl]-piperidinyl-4-carboxylic acid. M.p. 250° C. (Example 199);

1-[5,6-cyclohepteno-4-(3,4-methylenedioxybenzylamino)-[1]-benzothieno-[2,3-d]-pyrimidin-2-yl]-piperidinyl-4-carboxylic acid. M.p. 217° C. (Example 200);

1-[6-ethyl-4-(3,4-methylenedioxybenzylamino)-thieno-[2,3-d]-pyrimidin-2-yl]-piperidinyl-4-carboxylic acid (Example 201);

1-[6-chloro-4-(3,4-methylenedioxybenzylamino)-thieno-[2,3-d]-pyrimidin-2-yl]-piperidinyl-2-yl]-4-carboxylic acid (Example 202);

1-[5-chloro-6-methyl-4-(3,4-methylenedioxybenzylamino)-thieno-[2,3-d]-pyrimidin-2-yl]-piperidinyl-4-carboxylic acid, amorphous (Example 203);

1-[6-nitro-4-(3,4-methlendioxybenzylamino)-thieno-[2,3-d]-pyrimidin-2-yl]-piperidinyl-4-carboxylic acid, amorphous (Example 204);

1-[5,6-dimethyl-4-(3,4-methlenedioxybenzylamino)-thieno-[2,3-d]-pyrimidin-2-yl]-piperidinyl-4-carboxylic acid (Example 205);

1-[6-trifluoromethyl-4-(3,4-methylenedioxybenzylamino)-thieno-[2,3-d]-pyrimidin-2-yl]-piperidinyl-4-carboxylic acid (Example 206);

1-[6-methyl-4-(3-chloro-4-methoxybenzylamino)-thieno-[2,3-d]-pyrimidin-2-yl]-piperidinyl-4-carboxylic acid (Example 207);

1-[5-methyl-4-(3-chloro-4-methoxybenzylamino)-thieno-[2,3-d]-pyrimidin-2-yl]-piperidinyl-4-carboxylic acid (Example 208);

1-[5,6,7,8-tetrahydro-4-(3-chloro-4-methoxybenzylamino)-[1]-benzothieno-[2,3-d]-pyrimidin-2-yl]-piperidinyl-4-carboxylic acid sodium salt. M.p. 213° C. (Example 209);

1-[5,6-cyclopenteno-4-(3-chloro-4-methoxybenzylamino)-[1]-benzothieno-[2,3-d]-pyrimidin-2-yl]-piperidinyl-4-carboxylic acid sodium salt. M.p. 250° C.; potassium salt >250° C. (Example 210);

1-[5,6-cycloheptenо-4-(3-chloro-4-methoxybenzylamino)-[1]-benzothieno-[2,3-d]-pyrimidin-2-yl]-piperidinyl-4-carboxylic acid (Example 211);

1-[6-ethyl-4-(3-chloro-4-methoxybenzylamino)-thieno-[2,3-d]-pyrimidin-2-yl]-piperidinyl-4-carboxylic acid (Example 212);

1-[6-chloro-4-(3-chloro-4-methoxybenzylamino)-thieno-[2,3-d]-pyrimidin-2-yl]-piperidinyl-4-carboxylic acid (Example 213);

1-[5-chloro-6-methyl-4-(3-chloro-4-methoxybenzylamino)-thieno-[2,3-d]-pyrimidin-2-yl]-piperidinyl-4-carboxylic acid, sodium salt M.p. 250° C. (Example 214);

1-[6-nitro-4-(3-chloro-4-methoxybenzylamino)-thieno-[2,3-d]-pyrimidin-2-yl]-piperidinyl-4-carboxylic acid (Example 215);

1-[5,6-dimethyl-4-(3-chloro-4-methoxybenzylamino)-thieno-[2,3,-d]-pyrimidin-2-yl]-piperidinyl-4-carboxylic acid, sodium salt amorphous (Example 216);

1-[6-trifluoromethyl-4-(3-chloro-4-methoxybenzylamino)-thieno-[2,3-d]-pyrimidin-2-yl]-piperidinyl-4-carboxylic acid (Example 217);

1-[6-methyl-4-(3,4-dimethoxybenzylamino)-thieno-[2,3-d]-pyrimidin-2-yl]-piperidinyl-4-carboxylic acid (Example 218);

1-[5-methyl-4-(3,4-dimethoxybenzylamino)-thieno-[2,3-d]-pyrimidin-2-yl]-piperidinyl-4-carboxylic acid (Example 219);

1-[5,6,7,8-tetrahydro-4-(3,4-dimethoxybenzylamino)-[1]-benzothieno-[2,3-d]-pyrimidin-2-yl]-piperidinyl-4-carboxylic acid (Example 220);

1-[5,6-cyclopenteno-4-(3,4-dimethoxybenzylamino)-[1]-benzothieno-[2,3-d]-pyrimidin-2-yl]-piperidinyl-4-carboxylic acid (Example 221);

1-[5,6-cycloheptenо-4-(3,4-dimethoxybenzylamino)-[1]-benzothieno-[2,3-d]-pyrimidin-2-yl]-piperidinyl-4-carboxylic acid (Example 222);

1-[6-ethyl-4-(3,4-dimethoxybenzylamino)-thieno-[2,3-d]-pyrimidin-2-yl]-piperidinyl-4-carboxylic acid (Example 223);

1-[6-chloro-4-(3,4-dimethoxybenzylamino)-thieno-[2,3-d]-pyrimidin-2-yl]-piperidinyl-4-carboxylic acid (Example 224);

1-[5-chloro-6-methyl-4-(3,4-dimethoxybenzylamino)-thieno-[2,3-d]-pyrimidin-2-yl]-piperidinyl-4-carboxylic acid (Example 225);

1-[6-nitro-4-(3,4-dimethoxybenzylamino)-thieno-[2,3-d]-pyrimidin-2-yl]-piperidinyl-4-carboxylic acid (Example 226);

1-[5,6-dimethyl-4-(3,4-dimethoxybenzylamino)-thieno-[2,3-d]-pyrimidin-2-yl]-piperidinyl-4-carboxylic acid (Example 227);

1-[6-trifluoromethyl-4-(3,4-dimethoxybenzylamino)-thieno-[2,3-d]-pyrimidin-2-yl]-piperidinyl-4-carboxylic acid (Example 228);

1-[6-methyl-4-(3,4-dimethoxybenzylamino)-thieno-[2,3-d]-pyrimidin-2-yl]-piperidinyl-4-carboxylic acid (Example 229);

1-(6-methyl-4-benzylamino-thieno-[2,3-d]-pyrimidin-2-yl)-piperidinyl-4-carboxylic acid, M.p. 203° C. (Example 230);

1-(5-methyl-4-benzylamino-thieno-[2,3-d]-pyrimidin-2-yl)-piperidinyl-4-carboxylic acid, M.p. 203° C. (Example 231);

1-(5,6,7,8-tetrahydro-4-benzylamino-[1]-benzothieno-[2,3-d]-pyrimidin-2-yl)-piperidinyl-4-carboxylic acid (Example 232);

1-(5,6-cyclopenteno-4-benzylamino-[1]-benzothieno-[2,3-d]-pyrimidin-2-yl)-piperidinyl-4-carboxylic acid (Example 233);

1-(5,6-cycloheptenо-4-benzylamino-[1]-benzothieno-[2,3-d]-pyrimidin-2-yl)-piperidinyl-4-carboxylic acid M.p. 257° C. (Example 234);

1-(6-ethyl-4-benzylamino-thieno-[2.3-d]-pyrimidin-2-yl)-piperidinyl-4-carboxylic acid, sodium salt, amorphous (Example 235);

1-(6-chloro-4-benzylamino-thieno-[2,3-d]-pyrimidin-2-yl)-piperidinyl-4-carboxylic acid (Example 236);

1-(5-chloro-6-methyl-4-benzylamino-thieno-[2,3-d]-pyrimidin-2-yl)-piperidinyl-4-carboxylic acid (Example 237);

1-(6-nitro-4-benzylamino-thieno-[2,3-d]-pyrimidin-2-yl)-piperidinyl-4-carboxylic acid (Example 238);

1-(5,6-dimethyl-4-benzylamino-thieno-[2,3-d]-pyrimidin-2-yl)-piperidinyl-4-carboxylic acid (Example 239);

1-(6-trifluoromethyl-4-benzylamino-thieno-[2,3-d]-pyrimidin-2-yl)-piperidinyl-4-carboxylic acid (Example 240);

1-[6-methyl-4-(4-fluorobenzylamino)-thieno-[2,3-d]-pyrimidin-2-yl]-piperidinyl-4-carboxylic acid (Example 241);

1-[5-methyl-4-(4-fluorobenzylamino)-thieno-[2,3-d]-pyrimidin-2-yl]-piperidinyl-4-carboxylic acid (Example 242);

1-[5,6,7,8-tetrahydro-4-(4-fluorobenzylamino)-[1]-benzothieno-[2,3-d]-pyrimidin-2-yl]-piperidinyl-4-carboxylic acid, sodium salt, M.p. 279° C. (Example 243);

1-[5,6-cyclopenteno-4-(4-fluorobenzylamino)-[1]-benzothieno-[2,3-d]-pyrimidin-2-yl]-piperidinyl-4-carboxylic acid (Example 244);

1-[5,6-cycloheptenо-4-(4-fluorobenzylamino)-[1]-benzothieno-[2,3-d]-pyrimidin-2-yl]-piperidinyl-4-carboxylic acid (Example 245);

1-[6-ethyl-4-(4-fluorobenzylamino)-thieno-[2,3-d]-pyrimidin-2-yl]-piperidinyl-4-carboxylic acid (Example 246);

1-[6-chloro-4-94-fluorobenzylamino)-thieno-[2,3-d]-pyrimidin-2-yl]-piperidinyl-4-carboxylic acid (Example 247);

1-[5-chloro-6-methyl-4-(4-fluorobenzylamino)-thieno-2[2,3-d]-pyrimidin-2-yl]-piperidinyl-4-carboxylic acid (Example 248);

1-[6-nitro-4-(4-fluorobenzylamino)-thieno-[2,3-d]-pyrimidin-2-yl]-piperidinyl-4-carboxylic acid (Example 249);

1-[5,6-dimethyl-4-(4-fluorobenzylamino)-thieno-[2,3-d]-pyrimidin-2-yl]-piperidinyl-4-carboxylic acid (Example 250);

1-[6-trifluoromethyl-4-(4-fluorobenzylamino)-thieno-[2,3-d]-pyrimidin-2-yl]-piperidinyl-4-carboxylic acid (Example 251);

1-[6-methyl-4-(3,4-dichlorobenylamino)-thieno-[2,3-d]-pyrimidin-2-yl]-piperidinyl-4-carboxylic acid (Example 252);

1-[5-methyl-4-(3,4-dichlorobenzylamino)-thieno-[2,3-d]-pyrimidin-2-yl]-piperidinyl-4-carboxylic acid (Example 253);

1-[5,6,7,8-tetrahydro-4-(3,4-dichlorobenzylamino)-[1]-benzothieno-[2,3-d]-pyrimidin-2-yl]-piperidinyl-4-carboxylic acid (Example 254);

1-[5,6-cyclopenteno-4-(3,4-dichlorobenzylamino)-[1]-benzothieno-[2,3-d]-pyrimidin-2-yl]-piperidinyl-4-carboxylic acid (Example 255);

1-[5,6-cycloheptheno-4-(3,4-dichlorobenzylamino)-[1]-benzothieno-[2,3-d]-pyrimidin-2-yl]-piperidinyl-4-carboxylic acid (Example 256);

1-[6-ethyl-4-(3,4-dichlorobenzylamino)-thieno-[2,3-d]-pyrimidin-2-yl]-piperidinyl-4-carboxylic acid (Example 257);

1-[6-chloro-4-(3,4-dichlorobenzylamino)-thieno-[2,3-d]-pyrimidin-2-yl]-piperidinyl-4-carboxylic acid (Example 258);

1-[5-chloro-6-methyl-4-(3,4-dichlorobenzylamino)-thieno-[2,3-d]-pyrimidin-2-yl]-piperidinyl-4-carboxylic acid (Example 259);

1-[6-nitro-4-(3,4-dichlorobenzylamino)-thieno-[2,3-d]-pyrimidin-2-yl]-piperidinyl-4-carboxylic acid (Example 260);

1-[5,6-dimethyl-4-(3,4-dichlorobenzylamino)-thieno-[2,3-d]-pyrimidin-2-yl]-piperidinyl-4-carboxylic acid (Example 261);

1-[6-trifluoromethyl-4-(3,4-dichlorobenzylamino)-thieno-[2,3-d]-pyrimidin-2-yl]-piperidinyl-4-carboxylic acid (Example 262);

1-[6-methyl-4-(3-nitrobenzylamino)-thieno-[2,3-d]-pyrimidin-2-yl]-piperidinyl-4-carboxylic acid (Example 263);

1-[5-methyl-4-(3-nitrobenzylamino)-thieno-[2,3-d]-pyrimidin-2-yl]-piperidinyl-4-carboxylic acid (Example 264);

1-[5,6,7,8-tetrahydro-4-(3-nitrobenzylamino)-[1]-benzothieno-[2,3-d]-pyrimidin-2-yl]-piperidinyl-4-carboxylic acid (Example 265);

1-[5,6-cyclopenteno-4-(3-nitrobenzylamino)-[1]-benzothieno-[2,3-d]-pyrimidin-2-yl]-piperidinyl-4-carboxylic acid (Example 266);

1-[5,6-cycloheptheno-4-(3-nitrobenzylamino)-[1]-benzothieno-[2,3-d]-pyrimidin-2-yl]-piperidinyl-4-carboxylic acid (Example 267);

1-[6-ethyl-4-(3-nitrorobenzylamino)-thieno-[2,3-d]-pyrimidin-2-yl]-piperidinyl-4-carboxylic acid (Example 268);

1-[6-chloro-4-(3-nitrobenzylamino)-thieno-[2,3-d]-pyrimidin-2-yl]-piperidinyl-4-carboxylic acid (Example 269);

1-[5-chloro-6-methyl-4-(3-nitrobenzylamino)-thieno-[2,3-d]-pyrimidin-2-yl]-piperidinyl-4-carboxylic acid (Example 270);

1-[6-nitro-4-(3-nitrobenzylamino)-thieno-[2,3-d]-pyrimidin-2-yl]-piperidinyl-4-carboxylic acid (Example 271);

1-[5,6-dimethyl-4-(3-nitrobenzylamino)-thieno-[2,3-d]-pyrimidin-2-yl]-piperidinyl-4-carboxylic acid (Example 272);

1-[6-trifluoromethyl-4-(3-nitrobenzylamino)-thieno-[2,3-d]-pyrimidin-2yl]-piperidinyl-4-carboxylic acid (Example 273);

1-[6-methyl-4-(3,4-methylenedioxyphenethylamino)-thieno-[2,3-d]-pyrimidin-2-yl]-piperidinyl-4-carboxylic acid (Example 274);

1-[5-methyl-4-(3,4-methylenedioxyphenethylamino)-thieno-[2,3-d]-pyrimidin-2-yl]-piperidinyl-4-carboxylic acid (Example 275);

1-[5,6,7,8-tetrahydro-4-(3,4-methylenedioxyphenethylamino)-[1]-benzothieno-[2,3-d]-pyrimidin-2-yl]-piperidinyl-4-carboxylic acid (Example 276);

1-[5,6-cyclopenteno-4-(3,4-methylenedioxyphenethylamino)-[1]-benzothieno-[2,3-d]-pyrimidin-2-yl]-piperidinyl-4-carboxylic acid (Example 277);

1-[5,6-cycloheptheno-4-(3,4-methylenedioxyphenethylamino)-[1]-benzothieno-[2,3-d]-pyrimidin-2-yl]-piperidinyl-4-carboxylic acid (Example 278);

1-[6-ethyl-4-(3,4-methylenedioyphenethylamino)-thieno-[2,3-d]-pyrimidin-2-yl]-piperidinyl-4-carboxylic acid (Example 279);

1-[6-chloro-4-(3,4-methylenedioxyphenethylamino)-thieno-[2,3-d]-pyrimidin-2-yl]-piperidinyl-4-carboxylic acid (Example 280);

1-[5-chloro-6-methyl-4-(3,4-methylenedioxyphenethylamino)-thieno-[2,3-d]-pyrimidin-2-yl]-piperidinyl-4-carboxylic acid (Example 281);

1-[6-nitro-4-(3,4-methylenedioxyphenethylamino)-thieno-[2,3-d]-pyrimidin-2-yl]-piperidinyl-4-carboxylic acid (Example 282);

1-[5,6-dimethyl-4-(3,4-methylenedioxyphenethylamino)-thieno-[2,3-d]-pyrimidin-2-yl]-piperidinyl-4-carboxylic acid (Example 283);

1-[6-trifluoromethyl-4-(3,4-methylenedioxyphenethylamino)-thieno-[2,3-d]-pyrimidin-2-yl]-piperidinyl-4-carboxylic acid; (Example 284);

1-[6-methyl-4-(3,4-ethylenedioxyphenethylamino)-thieno-[2,3-d]-pyrimidin-2-yl]-piperidinyl-4-carboxylic acid (Example 285);

1-[5-methyl-4-(3,4-ethylenedioxyphenethylamino)-thieno-[2,3-d]-pyrimidin-2-yl]-piperidinyl-4-carboxylic acid (Example 286);

1-[5,6,7,8-tetrahydro-4-(3,4-ethylenedioxyphenethylamino)-[1]-benzothieno-[2,3-d]-pyrimidin-2-yl]-piperidinyl-4-carboxylic acid (Example 287);

1-[5,6-cyclopenteno-4-(3,4-ethylenedioxyphenethylamino)-[1]-benzothieno-[2,3-d]-pyrimidin-2-yl]-piperidinyl-4-carboxylic acid (Example 288);

1-[5,6-cycloheptheno-4-(3,4-ethylenedioxyphenethylamino)-[1]-benzothieno-[2,3-d]-pyrimidin-2-yl]-piperidinyl-4-carboxylic acid (Example 289);

1-[6-ethyl-4-(3,4-ethylenedioyphenethylamino)-thieno-[2,3-d]-pyrimidin-2-yl]-piperidinyl-4-carboxylic acid (Example 290);

1-[6-chloro-4-(3,4-ethylenedioxyphenethylamino)-thieno-[2,3-d]-pyrimidin-2-yl]-piperidinyl-4-carboxylic acid (Example 291);

1-[5-chloro-6-methyl-4-(3,4-ethylenedioxyphenethylamino)-thieno-[2,3-d]-pyrimidin-2-yl]-piperidinyl-4-carboxylic acid (Example 292);

1-[6-nitro-4-(3,4-ethylenedioxyphenethylamino)-thieno-[2,3-d]-pyrimidin-2-yl]-piperidinyl-4-carboxylic acid (Example 293);

1-[5,6-dimethyl-4-(3,4-ethylenedioxyphenethylamino)-thieno-[2,3-d]-pyrimidin-2-yl]-piperidinyl-4-carboxylic acid (Example 294);

1-[6-trifluoromethyl-4-(3,4-ethylenedioxyphenethylamino)-thieno-[2,3-d]-pyrimidin-2-yl]-piperidinyl-4-carboxylic acid; (Example 295);

EXAMPLE 296

2-Amino-5-methyl-3-ethoxycarbonyl-thiophene (5 g) and 4-cyanobenzoic acid methylester (2.7 g) are dissolved in dioxane (40 ml). Gaseous HCl is conducted through the solution for 5 hours. The usual workup yields 4-(3,4-dihydro-4-oxo-6-methyl-thieno-[2,3-d]-pyrimidin-2-yl]-benzoic acid methylester (6 g)

The replacement of the carbonyl group by Cl under the formation of an aromatic pyrimidine ring takes place under standard conditons.

A mixture of POCl$_3$ (18 ml) with 4-(3,4-dihydro-4-oxo-6-methyl-thieno-[2,3-d]-pyrimidin-2-yl)-benzoic acid methylester (6 g) is refluxed 4 hours under the addition of N,N-dimethylaniline (1.8 ml). The usual workup yields 4-(4-chloro-6-methyl-thieno-[2,3-d]-pyrimidin-2-yl)-benzoic acid methylester (5 g).

EXAMPLES 297–307

The procedure of Example 296 above can be employed to synthesize a variety of different compounds. Specifically, the reaction of 4-cyanbenzoic acid methylester and subsequent reaction with POCl$_3$ yields the following compounds from the referenced starting materials:

From 2-amino-4-methyl-3-ethoxycarbonyl-thiophene: 4-(4-chloro-5-methyl-thieno-[2,3-d]-pyrimidin-2-yl)-benzoic acid methylester (Example 297);
From 2-amino-4,5,6,7-tetrahydro-3-ethoxycarbonyl-benzothiophene: 4-(4-chloro-5,6,7,8-tetrahydro-[1]-benzothieno-[2,3-d]-pyrimidin-2-yl]-benzoic acid methylester (Example 298);
From 2-amino-4,5-cyclopenteno-3-ethoxycarbonyl-thiophene: 4-(4-chloro-5,6-cyclopenteno-thieno-[2,3-d]-pyrimidin-2-yl)-benzoic acid methylester (Example 299);
From 2-amino-4,5-cyclohepteno-3-ethoxycarbonyl-thiophene: 4-(4-chloro-5,6-cyclohepteno-thieno-[2,3-d]-pyrimidin-2-yl)-benzoic acid methylester (Example 300);
From 2-amino-5-ethyl-3-ethoxycarbonyl-thiophene: 4-(4-chloro-6-ethyl-thieno-[2,3-d]-pyrimidin-2-yl)-benzoic acid methylester (Example 301);
From 2-amino-5-propyl-3-ethoxycarbonyl-thiophene: 4-(4-chloro-6-propyl-thieno-[2,3-d]-pyrimidin-2-yl)-benzoic acid methylester (Example 302);
From 2-amino-5-chlor-3-ethoxycarbonyl-thiophene: 4-(4-chloro-6-chloro-thieno-[2,3-d]-pyrimidin-2-yl)-benzoic acid methylester (Example 303);
From 2-amino-4-chloro-5-methyl-3-ethoxycarbonyl-thiophene: 4-(4-chloro-5-chloro-6-methyl-thieno-[2,3-d]-pyrimidin-2-yl)-benzoic acid methylester (Example 304);
From 2-amino-5-nitro-3-ethoxycarbonyl-thiophene: 4-(4-chloro-6-nitro-thieno-[2,3-d]-pyrimidin-2-yl)-benzoic acid methylester (Example 305);
From 2-amino-4,5-dimethyl-3-ethoxycarbonyl-thiophene: 4-(4-chloro-5,6-dimethyl-thieno-[2,3-d]-pyrimidin-2-yl)-benzoic acid methylester (Example 306);
From 2-amino-5-trifluoromethyl-3-ethoxycarbonyl-thiophene: 4-(4-chloro-6-trifluoromethyl-thieno-[2,3-d]-pyrimidin-2-yl)-benzoic acid methylester (Example 307);

EXAMPLE 308

The reaction procedure as above wherein 3,4-methylenedioxy-benzylamine is reacted with 4-(4-chloro-6-methyl-thieno-[2,3-d]-pyrimidin-2-yl)-benzoic acid methylester yields 4-[4-(3,4-methylenedioxybenzylamino)-6-methyl-thieno-[2,3-d]-pyrimidin-2-yl]-benzoic acid methylester.

EXAMPLE 309

The reaction procedure as above wherein 3,4-methylenedioxy-benzylamine is reacted with 4-(4-chloro-5-methyl-thieno-[2,3-d]-pyrimidin-2-yl)-benzoic acid methylester yields 4-[4-(3,4-methylenedioxybenzylamino)-5-methyl-thieno-[2,3-d]-pyrimidin-2-yl]-benzoic acid methylester.

EXAMPLE 310

The reaction procedure as above wherein 3,4-methylenedioxy-benzylamine is reacted with 4-(4-chloro-5,6,7,8-tetrahydro-[1]-benzothieno-[2,3-d]-pyrimidin-2-yl)-benzoic acid methylester yields 4-[4-(3,4-methylenedioxybenzylamino)-5,6,7,8-tetrahydro-[1]-benzothieno-[2,3-d]-pyrimidin-2-yl]-benzoic acid methylester, m.p. 198° C.

EXAMPLE 311

The reaction procedure as above wherein 3,4-methylenedioxy-benzylamine is reacted with 4-(4-chloro-5,6-cyclopenteno-thieno-[2,3-d]-pyrimidin-2-yl)-benzoic acid methylester yields 4-[4-(3,4-methylenedioxybenzylamino)-5,6-cyclopenteno-thieno-[2,3-d]-pyrimidin-2-yl]-benzoic acid methylester.

EXAMPLE 312

The reaction procedure as above wherein 3,4-methylenedioxy-benzylamine is reacted with 4-(4-chloro-5,6-cyclohepteno-thieno-[2,3-d]-pyrimidin-21yl)-benzoic acid methylester yields 4-[4-(3,4-methylenedioxybenzylamino0-5,6-cyclohepteno-thieno-[2,3-d]-pyrimidin-2-yl]-benzoic acid methylester.

EXAMPLE 313

The reaction procedure as above wherein 3,4-methylenedioxy-benzylamine is reacted with 4-(4-chloro-6-ethyl-thieno-[2,3-d]-pyrimidin-2-yl0-benzoic acid methylester yields 4-[4-(3,4-methylenedioxybenzylamino)-6-ethyl-thieno-[2,3-d]-pyrimidin-2-yl]-benzoic acid methylester.

EXAMPLE 314

The reaction procedure as above wherein 3,4-methylenedioxy-benzylamine is reacted with 4-(4-chloro-6-propyl-thieno-[2,3-d]-pyrimidin-2-yl)-benzoic acid methylester yields 4-[4-(3,4-methylenedioxybenzylamino)-6-propyl-thieno-[2,3-d]-pyrimidin-2-yl]-benzoic acid methylester

EXAMPLE 315

The reaction procedure as above wherein 3,4-methylenedioxy-benzylamine is reacted with 4-(4-chloro-6-chloro-thieno-[2,3-d]-pyrimidin-2-yl)-benzoic acid methylester yields 4-[4-(3,4-methylenedioxybenzylamino)-6-chloro-thieno-[2,3-d]-pyrimidin-21-yl]-benzoic acid methylester.

EXAMPLE 316

The reaction procedure as above wherein 3,4-methylenedioxy-benzylamine is reacted with 4-(4-chloro-5-chloro-6-methyl-thieno-[2,3-d]-pyrimidin-2-yl0-benzoic acid methylester yields 4-[4-(3,4-methylenedioxybenzylamino)-5-chloro-6-methyl-thieno-[2,3-d]-pyrimidin-2-yl]-benzoic acid methylester.

EXAMPLE 317

The reaction procedure as above wherein 3,4-methylenedioxy-benzylamine is reacted with 4-(4-chloro-6- nitro-thieno-[2,3-d]-pyrimidin-2-yl)-benzoic acid methylester yields 4-[4(3,4-methylenedioxybenzylamino)-6-nitro-thieno-[2,3-d]-pyrimidin-2-yl]-benzoic acid methylester.

EXAMPLE 318

The reaction procedure as above wherein 3,4-methylenedioxy-benzylamine is reacted with 4-(4-chloro-5,6-dimethyl-thieno-[2,3-d]-pyrimidin-2-yl)-benzoic acid methylester yields 4-[4-(3,4-methylenedioxybenzylamino)-5,6-dimethyl-thieno-[2,3-d]-pyrimidin-2-yl]-benzoic acid methylester.

EXAMPLE 319

The reaction procedure as above wherein 3,4-methylenedioxy-benzylamine is reacted with 4-(4-chloro-6-trifluoromethyl-thieno-[2,3-d]-pyrimidin-2-yl)-benzoic acid methylester yields 4-[4-(3,4-methylenedioxybenzylamino)-6-trifluoromethyl-thieno-[2,3-d]-pyrimidin-2-yl]-benzoic acid methylester.

EXAMPLE 320

The reaction of 3-chloro-4-methoxy-benzylamine with 4-(4-chloro-6-methyl-thieno-[2,3-d]-pyrimidin-2-yl)-benzoic acid methylester yields 4-[4-(3-chloro-4-methoxybenzylamino)-6-methyl-thieno-[2,3-d]-pyrimidin-2-yl]-benzoic acid methylester.

EXAMPLE 321

The reaction procedure as above wherein 3,4-methylenedioxy-benzylamine is reacted with 4-(4-chloro-5-methyl-thieno-[2,3-d]-pyrimidin-2-yl)-benzoic acid methylester yields 4-[4-(3-chloro-4-methoxybenzylamino)-5-methyl-thieno-[2,3-d]-pyrimidin-2-yl]-benzoic acid methylester.

EXAMPLE 322

The reaction procedure as above wherein 3,4-methylenedioxy-benzylamine is reacted with 4-(4-chloro-5,6,7,8-tetrahydro-[1]-benzothieno-[2,3-d]-pyrimidin-2-yl)-benzoic acid methylester yields 4-[4-(3-chloro-4-methoxybenzylamino)-5,6,7,8-tetrahydro-[1]-benzothieno-[2,3,-d]-pyrimidin-2-yl]-benzoic acid methylester.

EXAMPLE 323

The reaction procedure as above wherein 3,4-methylenedioxy-benzylamine is reacted with 4-(4-chloro-5,6,-cyclopenteno-thieno-[2,3-d]-pyrimidin-2-yl)-benzoic acid methylester yields 4-[4-(3-chloro-4-methoxybenzylamino)-5,6-cyclopenteno-thieno-[2,3-d]-pyrimidin-2-yl]-benzoic acid methylester.

EXAMPLE 324

The reaction procedure as above wherein 3,4-methylenedioxy-benzylamine is reacted with 4-(4-chloro-6-ethyl-thieno-[2,3-d]-pyrimidin-2-yl)-benzoic acid methylester yields 4-[4-(3-chloro-4-methoxybenzylamino0-6-ethyl-thieno-[2,3-d]-pyrimidin-2-yl]-benzoic acid methylester.

EXAMPLE 325

The reaction procedure as above wherein 3,4-methylenedioxy-benzylamine is reacted with 4-(4-chloro-6-chloro-thieno-[2,3-d]-pyrimidin-2-yl)-benzoic acid methylester yields 4-[4-(3-chloro-4-methoxybenzylamino)-6-chloro-thieno-[2,3-d]-pyrimidin-2-yl]-benzoic acid methylester.

EXAMPLE 326

The reaction procedure as above wherein 3,4-methylenedioxy-benzylamine is reacted with 4-(4-chloro-5-chloro-6-methyl-thieno-[2,3-d]-pyrimidin-2-yl0-benzoic acid methylester yields 4-[4-(3-chloro-4-methoxybenzylamino)-5-chloro-6-methyl-thieno-[2,3-d]-pyrimidin-2-yl]-benzoic acid methylester.

EXAMPLE 327

The reaction procedure as above wherein 3,4-methylenedioxy-benzylamine is reacted with 4-(4-chloro-6-nitro-thieno-[2,3-d]-pyrimidin-2-yl)-benzoic acid methylester yields 4-[4-(3-chloro-4-methoxybenzylamino)-6-nitro-thieno-[2,3-d]-pyrimidin-2-yl]-benzoic acid methylester.

EXAMPLE 328

The reaction procedure as above wherein 3,4-methylenedioxy-benzylamine is reacted with 4-(4-chloro-5,6-dimethyl-thieno-[2,3-d]-pyrimidin-2-yl)-benzoic acid methylester yields 4-[4-(3-chloro-4-methoxybenzylamino)-5,6-dimethyl-thieno-[2,3-d]-pyrimidin-2-yl]-benzoic acid methylester.

EXAMPLE 329

The reaction procedure as above wherein 3,4-methylenedioxy-benzylamine is reacted with 4-(4-chloro-6-trifluoromethyl-thieno-[2,3-d]-pyrimidin-2-yl)-benzoic acid methylester yields 4-[4-(3-chloro-4-methoxybenzylamino)-6-trifluoromethyl-thieno-[2,3-d]-pyrimidin-2-yl]-benzoic acid methylester.

EXAMPLE 330

The reaction procedure as above wherein 3,4-dimethoxy-benzylamine is reacted with 4-(4-chloro-6-methyl-thieno-[2,3-d]-pyrimidin-2-yl)-benzoic acid methylester yields 4-[4-(3,4-dimethoxybenzylamino)-6-methyl-thieno-[2,3-d]-pyrimidin-2-yl]-benzoic acid methylester.

EXAMPLE 331

The reaction procedure as above wherein 3,4-dimethoxy-benzylamine is reacted with 4-(4-chloro-5-methyl-thieno-[2,3-d]-pyrimidin-2-yl)-benzoic acid methylester yields 4-[4-(3,4-dimethoxybenzylamino)-5-methyl-thieno-[2,3-d]-pyrimidin-2-yl]-benzoic acid methylester.

EXAMPLE 332

The reaction procedure as above wherein 3,4-dimethoxy-benzylamine is reacted with 4-(4-chloro-5,6,7,8-tetrahydro-[1]-benzothieno-[2,3-d]-pyrimidin-2-yl)-benzoic acid methylester yields 4-[4-(3,4-dimethoxybenzylamino)-5,6,7,8-tetrahydro-[1]-benzothieno-[2,3-d]-pyrimidin-2-yl]-benzoic acid methylester

EXAMPLE 333

The reaction procedure as above wherein 3,4-dimethoxy-benzylamine is reacted with 4-(4-chloro-5,6-cyclopenteno-thieno-[2,3-d]-pyrimidin-2-yl)-benzoic acid methylester yields 4-[4-(3,4-dimethoxybenzylamino)-5,6-cyclopenteno-thieno-[2,3-d]-pyrimidin-2-yl]-benzoic acid methylester.

EXAMPLE 334

The reaction procedure as above wherein 3,4-dimethoxybenzylamine is reacted with 4-(4-chloro-5,6-cyclohepteno-thieno-[2,3-d]-pyrimidin-2-yl)-benzoic acid methylester yields 4-[4-(3,4-dimethoxybenzylamino0-5,6-cyclohepteno-thieno-[2,3-d]-pyrimidin-2-yl]-benzoic acid methylester.

EXAMPLE 335

The reaction procedure as above wherein 3,4-dimethoxybenzylamine is reacted with 4-(4-chloro-6-ethyl-thieno-[2,3-d]-pyrimidin-2-yl)-benzoic acid methylester yields 4-[4-(3,4-dimethoxybenzylamino)-6-ethyl-thieno-[2,3-d]-pyrimidin-2-yl]-benzoic acid methylester.

EXAMPLE 336

The reaction procedure as above wherein 3,4-dimethoxybenzylamine is reacted with 4-(4-chloro-6-chloro-thieno-[2,3-d]-pyrimidin-2-yl)-benzoic acid methylester yields 4-[4-(3,4-dimethoxybenzylamino)-6-chloro-thieno-[2,3-d]-pyrimidin-2-yl]-benzoic acid methylester.

EXAMPLE 337

The reaction procedure as above wherein 3,4-dimethoxybenzylamine is reacted with 4-(4-chloro-5-chloro-6-methyl-thieno-[2,3-d]-pyrimidin-2-yl)-benzoic acid methylester yields 4-[4-(3,4-dimethoxybenzylamino)-5-chloro-6-methyl-thieno-[2,3-d]-pyrimidin-2-yl]-benzoic acid methylester

EXAMPLE 338

The reaction procedure as above wherein 3,4-dimethoxybenzylamine is reacted with 4-(4-chloro-6-nitro-thieno-[2,3-d]-pyrimidin-2-yl)-benzoic acid methylester yields 4-[4-(3,4-dimethoxybenzylamino)-6-nitro-thieno-[2,3-d]-pyrimidin-2-yl]-benzoic acid methylester.

EXAMPLE 339

The reaction procedure as above wherein 3,4-dimethoxybenzylamine is reacted with 4-(4-chloro-5,6-dimethyl-thieno-[2,3-d]-pyrimidin-2-yl)-benzoic acid methylester yields 4-[4-(3,4-dimethoxybenzylamino)-5,6-dimethyl-thieno-[2,3-d]-pyrimidin-2-yl]-benzoic acid methylester.

EXAMPLE 340

The reaction procedure as above wherein 3,4-dimethoxybenzylamine is reacted with 4-(4-chloro-6-trifluoromethyl-thieno-[2,3-d]-pyrimidin-2-yl)-benzoic acid methylester yields 4-[4-(3,4-dimethoxybenzylamino)-6-trifluoromethyl-thieno-[2,3-d]-pyrimidin-2-yl]-benzoic acid methylester

EXAMPLE 341

The reaction procedure as above wherein benzylamine is reacted with 4-(4-chloro-6-methyl-thieno-[2,3-d]-pyrimidin-2-yl]-benzoic acid methylester yields 4-(4-benzylamino-6-methyl-thieno-[2,3-d]-pyrimidin-2-yl)-benzoic acid methylester.

EXAMPLE 342

The reaction procedure as above wherein benzylamine is reacted with 4-(4-chloro-5-methyl-thieno-[2,3-d]-pyrimidin-2-yl]-benzoic acid methylester yields 4-(4-benzylamino-5-methyl-thieno-[2,3-d]-pyrimidin-2-yl)-benzoic acid methylester.

EXAMPLE 343

The reaction procedure as above wherein benzylamine is reacted with 4-(4-chloro-5,6,7,8-tetrahydro-[1]-benzothieno-[2,3-d]-pyrimidin-2-yl]-benzoic acid methylester yields 4-(4-benzylamino-5,6,7,8-tetrahydro-[1]-benzothieno-[2,3-d]-pyrimidin-2-yl)-benzoic acid methylester.

EXAMPLE 344

The reaction procedure as above wherein benzylamine is reacted with 4-(4-chloro-5,6-cyclopenteno-thieno-[2,3-d]-pyrimidin-2-yl]-benzoic acid methylester yields 4-(4-benzylamino-5,6-cyclopenteno-thieno-[2,3-d]-pyrimidin-2-yl)-benzoic acid methylester.

EXAMPLE 345

The reaction procedure as above wherein benzylamine is reacted with 4-(4-chloro-5,6-cyclohepteno-thieno-[2,3-d]-pyrimidin-2-yl]-benzoic acid methylester yields 4-(4-benzylamino-5,6-cyclopenteno-thieno-[2,3-d]-pyrimidin-2-yl)-benzoic acid methylester.

EXAMPLE 346

The reaction procedure as above wherein benzylamine is reacted with 4-(4-chloro-6-ethyl-thieno-[2,3-d]-pyrimidin-2-yl]-benzoic acid methylester yields 4-(4-benzylamino-6-ethyl-thieno-[2,3-d]-pyrimidin-2-yl)-benzoic acid methylester.

EXAMPLE 347

The reaction procedure as above wherein benzylamine is reacted with 4-(4-chloro-6-chloro-thieno-[2,3-d]-benzoic acid methylester yields 4-(4-benzylamino-6-chloro-thieno-[2,3-d]-pyrimidin-2-yl)-benzoic acid methylester.

EXAMPLE 348

The reaction procedure as above wherein benzylamine is reacted with 4-(4-chloro-5-chloro-6-methyl-thieno-[2,3-d]-[pyrimidin-2-yl)-benzoic acid methylester yields 4-(4-benzylamino-5-chloro-6-methyl-thieno-[2,3-d]-pyrimidin-2-yl)-benzoic acid methylester.

EXAMPLE 349

The reaction procedure as above wherein benzylamine is reacted with 4-(4-chloro-6-nitro-thieno-[2,3-d]-pyrimidin-2-yl)-benzoic acid methylester yields 4-(4-benzylamino-6-nitro-thieno-[2,3-d]-pyrimidin-2-yl)-benzoic acid methylester.

EXAMPLE 350

The reaction procedure as above wherein benzylamine is reacted with 4-(4-chloro-5,6-dimethyl-thieno-[2,3-d]-pyrimidin-2-yl)-benzoic acid methylester yields 4-(4-benzylarino-5,6-dimethyl-thieno-[2,3-d]-pyrimidin-2-yl)-benzoic acid methylester.

EXAMPLE 351

The reaction procedure as above wherein benzylamine is reacted with 4-(4-chloro-6-trifluoromethyl-thieno-[2,3-d]-pyrimidin-2-yl)-benzoic acid methylester yields 4-(4-benzylamino-6-trifluoromethyl-thieno-[2,3-d]-pyrimidin-2-yl)-benzoic acid methylester.

EXAMPLE 352

The reaction procedure as above wherein 4-fluorobenzylamine is reacted with 4-(4-chloro-6-methylthieno-[2,3-d]-pyrimidin-2-yl)-benzoic acid methylester yields 4-[4-(4-fluorobenzylamino)-6-methyl-thieno-[2,3-d]-pyrimidin-2-yl]-benzoic acid methylester.

EXAMPLE 353

The reaction procedure as above wherein 4-fluorobenzylamine is reacted with 4-(4-chloro-5-methyl-thieno-[2,3-d]-pyrimidin-2-yl)-benzoic acid methylester yields 4-[4-(4-fluorobenzylamino)-5-methyl-thieno-[2,3-d]-pyrimidin-2-yl]-benzoic acid methylester.

EXAMPLE 354

The reaction procedure as above wherein 4-fluorobenzylamine is reacted with 4-(4-chloro-5,6,7,8-tetrahydro-[1]-benzothieno-[2,3-d]-pyrimidin-2-yl)-benzoic acid methylester yields 4-[4-(4-fluorobenzylamino)-5,6,7,8-tetrahydro-[1]-benzothieno-[2,3-d]-pyrimidin-2-yl]-benzoic acid methylester.

EXAMPLE 355

The reaction procedure as above wherein 4-fluorobenzylamine is reacted with 4-(4-chloro-5,6-cyclopenteno-thieno-[2,3-d]-pyrimidin-2-yl)-benzoic acid methylester yields 4-[4-(4-fluorobenzylamino)-5,6-cyclopenteno-thieno-[2,3-d]-pyrimidin-2-yl]-benzoic acid methylester.

EXAMPLE 356

The reaction procedure as above wherein 4-fluorobenzylamine is reacted with 4(4-chloro-5,6-cyclohepteno-thieno-[2,3-d]-pyrimidin-2-yl)-benzoic acid methylester yields 4-[4-(4-fluorobenzylamino)-5,6-cyclopenteno-thieno-[2,3-d]-pyrimidin-2-yl]-benzoic acid methylester.

EXAMPLE 357

The reaction procedure as above wherein 4-fluorobenzylamine is reacted with 4-(4-chloro-6-ethyl-thieno-[2,3-d]-pyrimidin-2-yl)-benzoic acid methylester yields 4-[4-(4-fluorobenzylamino)-6-ethyl-thieno-[2,3-d]-pyrimidin-2-yl]-benzoic acid methylester.

EXAMPLE 358

The reaction procedure as above wherein 4-fluorobenzylamine is reacted with 4-(4-chloro-6-chloro-thieno-[2,3-d]-pyrimidin-2-yl)-benzoic acid methylester yields 4-[4-(4-fluorobenzylamino)-6-chloro-thieno-[2,3-d]-pyrimidin-2-yl]-benzoic acid methylester.

EXAMPLE 359

The reaction procedure as above wherein 4-fluorobenzylamine is reacted with 4-(4-chloro-5-chloro-6-methyl-thieno-[2,3-d]-pyrimidin-2-yl)-benzoic acid methylester yields 4-[4-(4-fluorobenzylamino)-5-chloro-6-methyl-thieno-[2,3-d]-pyrimidin-2-yl]-benzoic acid methylester.

EXAMPLE 360

The reaction procedure as above wherein 4-fluorobenzylamine is reacted with 4-(4-chloro-6-nitro-thieno-[2,3-d]-pyrimidin-2-yl)-benzoic acid methylester yields 4-[4-(4-fluorobenzylamino)-6-nitro-thieno-[2,3-d]-pyrimidin-2-yl]-benzoic acid methylester.

EXAMPLE 361

The reaction procedure as above wherein 4-fluorobenzylamine is reacted with 4-(4-chloro-5,6-dimethyl-thieno-[2,3-d]-pyrimidin-2-yl)-benzoic acid methylester yields 4-[4-(4-fluorobenzylamino)-5,6-dimethyl-thieno-[2,3-d]-pyrimidin-2-yl]-benzoic acid methylester.

EXAMPLE 362

The reaction procedure as above wherein 4-fluorobenzylamine is reacted with 4-(4-chloro-6-trifluoromethyl-thieno-[2,3-d]-pyrimidin-2-yl)-benzoic acid methylester yields 4-[4-(4-fluorobenzylamino)-6-trifluoromethyl-thieno-[2,3-d]-pyrimidin-2-yl]-benzoic acid methylester.

EXAMPLE 363

The reaction procedure as above wherein 3,4-dichlorobenzylamine is reacted with 4-(4-chloro-6-methyl-thieno-[2,3-d]-pyrimidin-2-yl)-benzoic acid methylester yields 4-[4-(3,4-dichlorobenzylamino)-6-methyl-thieno-[2,3-d]-pyrimidin-2-yl]-benzoic acid methylester.

EXAMPLE 364

The reaction procedure as above wherein 3,4-dichlorobenzylamine is reacted with 4-(4-chloro-5-methyl-thieno-[2,3-d]-pyrimidin-2-yl)-benzoic acid methylester yields 4-[4-(3,4-dichlorobenzylamino)-5-methyl-thieno-[2,3-d]-pyrimidin-2-yl]-benzoic acid methylester.

EXAMPLE 365

The reaction procedure as above wherein 3,4-dichlorobenzylamine is reacted with 4-(4-chloro-5,6,7,8-tetrahydro-[1]-benzothieno-[2,3-d]-pyrimidin-2-yl)-benzoic acid methylester yields 4-[4-(3,4-dichlorobenzylamino)-5,6,7,8-tetrahydro-[1]-benzothieno-[2,3-d]-pyrimidin-2-yl]-benzoic acid methylester

EXAMPLE 366

The reaction procedure as above wherein 3,4-dichlorobenzylamine is reacted with 4-(4-chloro-5,6-cyclopenteno-thieno-[2,3-d]-pyrimidin-2-yl)-benzoic acid methylester yields 4-[4-(3,4-dichlorobenzylamino)-5,6-cyclopenteno-thieno-[2,3-d]-pyrimidin-2-yl]-benzoic acid methylester.

EXAMPLE 367

The reaction procedure as above wherein 3,4-dichlorobenzylamine is reacted with 4-(4-chloro-5,6-cyclohepteno-thieno-[2,3-d]-pyrimidin-2-yl)-benzoic acid methylester yields 4-[4-(3,4-dichlorobenzylamino)-5,6-cyclohepteno-thieno-[2,3-d]-pyrimidin-2-yl]-benzoic acid methylester.

EXAMPLE 368

The reaction procedure as above wherein 3,4-dichlorobenzylamine is reacted with 4-(4-chloro-6-ethyl-thieno-[2,3-d]-pyrimidin-2-yl)-benzoic acid methylester yields 4-[4-(3,4-dichlorobenzylamino)-6-ethyl-thieno-[2,3-d]-pyrimidin-2-yl]-benzoic acid methylester.

EXAMPLE 369

The reaction procedure as above in wherein 3,4-dichlorobenzylamine is reacted with 4-(4-chloro-6-chlorothieno-[2,3-d]-pyrimidin-2-yl)-benzoic acid methylester yields 4-[4-(3,4-dichlorobenzylamino)-6-chloro-thieno-[2,3-d]-pyrimidin-2-yl]-benzoic acid methylester

EXAMPLE 370

The reaction procedure as above wherein 3,4-dichlorobenzylamine is reacted with 4-(4-chloro-5-chloro-6-methyl-thieno-[2,3-d]-pyrimidin-2-yl)-benzoic acid methylester yields 4-[4-(3,4-dichlorobenzylamino)-5-chloro-6-methyl-thieno-[2,3-d]-pyrimidin-2-yl]-benzoic acid methylester.

EXAMPLE 371

The reaction procedure as above wherein 3,4-dichlorobenzylamine is reacted with 4-(4-chloro-6-nitro-thieno-[2,3-d]-pyrimidin-2-yl)-benzoic acid methylester yields 4-[4-(3,4-dichlorobenzylamino)-6-nitro-thieno-[2,3-d]-pyrimidin-2-yl]-benzoic acid methylester.

EXAMPLE 372

The reaction procedure as above wherein 3,4-dichlorobenzylamine is reacted with 4-(4-chloro-5,6-dimethyl-thieno-[2,3-d]-pyrimidin-2-yl)-benzoic acid methylester yields 4-[4-(3,4-dichlorobenzylamino)-5,6-dimethyl-thieno-[2,3-d]-pyrimidin-2-yl]-benzoic acid methylester.

EXAMPLE 373

The reaction procedure as above wherein 3,4-dichlorobenzylamine is reacted with 4-(4-chloro-6-trifluoromethyl-thieno-[2,3-d]-pyrimidin-2-yl)-benzoic acid methylester yields 4-[4-(3,4-dichlorobenzylamino)-6-trifluoromethyl-thieno-[2,3-d]-pyrimidin-2-yl]-benzoic acid methylester.

EXAMPLE 374

The reaction procedure as above wherein 3-nitrobenzylamine is reacted with 4-(4-chloro-6-methyl-thieno-[2,3-d]-pyrimidin-2-yl)-benzoic acid methylester yields 4-[4-(3-nitrobenzylamino)-6-methyl-thieno-[2,3-d]-pyrimidin-2-yl]-benzoic acid methylester.

EXAMPLE 375

The reaction procedure as above wherein 3-nitrobenzylamine is reacted with 4-(4-chloro-5-methyl-thieno-[2,3-d]-pyrimidin-2yl)-benzoic acid methylester yields 4-[4-(3-nitrobenzylamino)-5-methyl-thieno-[2,3-d]-pyrimidin-2-yl]-benzoic acid methylester.

EXAMPLE 376

The reaction procedure as above wherein 3-nitrobenzylamine is reacted with 4-(4-chloro-5,6,7,8,-tetrahydro-[1]-benzothieno-[2,3-d]-pyrimidin-2-yl)-benzoic acid methylester yields 4-[4-(3-nitrobenzylamino)-5,6,7,8-tetrahydro-[1]-benzothieno-[2,3-d]-pyrimidin-2-yl]-benzoic acid methylester.

EXAMPLE 377

The reaction procedure as above wherein 3-nitrobenzylamine is reacted with 4-(4-chloro-5,6-cyclopenteno-thino-[2,3-d]-pyrimidin-2-yl)-benzoic acid methylester yields 4-[4-3(nitrobenzylamino)-5,6-cyclopenteno-thieno-[2,3-d]-pyrimidin-2-yl]-benzoic acid methylester.

EXAMPLE 378

The reaction procedure as above wherein 3-nitrobenzylamine is reacted with 4-(4-chloro-5,6-cyclohepteno-thieno-[2,3-d]-pyrimidin-2-yl)-benzoic acid methylester yields 4-[4-(3-nitrobenzylamino)-5,6-cyclohepteno-thieno-[2,3-d]-pyrimidin-2-yl]-benzoic acid methylester.

EXAMPLE 379

The reaction procedure as above wherein 3-nitrobenzylamine is reacted with 4-(4-chloro-6-ethyl-thieno-[2,3-d]-pyrimidin-2-yl)-benzoic acid methylester yields 4-[4-(3-nitrobenzylamino)-6-ethyl-thieno-[2,3-d]-pyrimidin-2-yl]-benzoic acid methylester.

EXAMPLE 380

The reaction procedure as above wherein 3-nitrobenzylamine is reacted with 4-(4-chloro-6-chloro-thieno-[2,3-d]-pyrimidin-2-yl)-benzoic acid methylester yields 4-[4-(3-nitrobenzylamino)-6-chloro-thieno-[2,3-d]-pyrimidin-2-yl]-benzoic acid methylester.

EXAMPLE 381

The reaction procedure as above wherein 3-nitrobenzylamine is reacted with 4-(4-chloro-5-chloro-6-methyl-thieno-[2,3-d]-pyrimidin-2-yl)-benzoic acid methylester yields 4-[4-(3-nitrobenzylamino)-5-chloro-6-methyl-thieno-[2,3-d]-pyrimidin-2-yl]-benzoic acid methylester.

EXAMPLE 382

The reaction procedure as above wherein 3-nitrobenzylamine is reacted with 4-(4-chloro-6-nitro-thieno-[2,3-d]-pyrimidin-2-yl)-benzoic acid methylester yields 4-[4-(3-nitrobenzylamino)-6-nitro-thieno-[2,3-d]-pyrimidin-2-yl]-benzoic acid methylester.

EXAMPLE 383

The reaction procedure as above wherein 3,4-methylenedioxyphenethylamine is reacted with 4-(4-chloro-6-ethyl-thieno-[2,3-d]-pyrimidin-2-yl)-benzoic acid methylester yields 4-[4-3,4-methylenedioxyphenethylamino)-6-ethyl-thieno-[2,3-d]-pyrimidin-2-yl]-benzoic acid methylester.

EXAMPLE 384

The reaction procedure as above wherein 3,4-methylenedioxyphenethylamine is reacted with 4-(4-chloro-6-chloro-thieno-[2,3-d]-pyrimidin-2-yl)-benzoic acid methylester yields 4-[4-(3,4-methylenedioxyphenethylamino)-6-chloro-thieno-[2,3-d]-pyrimidin-2-yl]-benzoic acid methylester.

EXAMPLE 385

The reaction procedure as above in wherein 3,4-methylenedioxyphenethylamine is reacted with 4-(4-chloro-5-chloro-6-methyl-thieno-[2,3-d]-pyrimidin-2-yl)-benzoic acid methylester yields 4-[4-(3,4-methylenedioxyphenethylamino)-5-chloro-6-methyl-thieno-[2,3-d]-pyrimidin-2-yl]-benzoic acid methylester.

EXAMPLE 386

The reaction procedure as above wherein 3,4-methylenedioxyphenethylamine is reacted with 4-(4-chloro- 6-nitro-thieno-[2,3-d]-pyrimidin-2-yl)-benzoic acid methylester yields 4-[4-(3,4-methylenedioxyphenethylamino)-6-nitro-thieno-[2,3-d]-pyrimidin-2-yl]-benzoic acid methylester.

EXAMPLE 387

The reaction procedure as above wherein 3,4-methylenedioxyphenethylamine is reacted with 4-(4-chloro-5,6-dimethyl-thieno-[2,3-d]-pyrimidin-2-yl)-benzoic acid methylester yields 4-[4-(3,4-methylenedioxyphenethylamino)-5,6-dimethyl-thieno-[2,3-d]-pyrimidin-2-yl]-benzoic acid methylester.

EXAMPLE 388

The reaction procedure as above wherein 3,4-methylenedioxyphenethylamine is reacted with 4-(4-chloro-6-trifluoromethyl-thieno-[2,3-d]-pyrimidin-2-yl)-benzoic acid methylester yields 4-[4-(3,4-methylenedioxyphenethylamino)-6-trifluoromethyl-thieno-[2,3-d]-pyrimidin-2-yl]-benzoic acid methylester.

EXAMPLE 389

The reaction procedure as above wherein 3,4-ethylenedioxybenzylamine is reacted with 4-(4-chloro-6-methyl-thieno-[2,3-d]-pyrimidin-2-yl)-benzoic acid methylester yields 4-[4-(3,4-ethylenedioxyphenethylamino)-6-methyl-thieno-[2,3-d]-pyrimidin-2-yl]-benzoic acid methylester.

EXAMPLE 390

The reaction procedure as above wherein 3,4-ethylenedioxybenzylamine is reacted with 4-(4-chloro-5-methyl-thieno-[2,3-d]-pyrimidin-2-yl)-benzoic acid methylester yields 4-[4-(3,4-ethylenedioxyphenethylamino)-5-methyl-thieno-[2,3-d]-pyrimidin-2-yl]-benzoic acid methylester.

EXAMPLE 391

The reaction procedure as above wherein 3,4-ethylenedioxybenzylamine is reacted with 4-(4-chloro-5,6,7,8-tetrahydro-[1]-benzothieno-[2,3-d]-pyrimidin-2-yl)-benzoic acid methylester yields 4-[4-(3,4-ethylenedioxyphenethylamino)-5,6,7,8-tetrahydro-[1]-benzothieno-[2,3-d]-pyrimidin-2-yl]-benzoic acid methylester.

EXAMPLE 392

The reaction procedure as above wherein 3,4-ethylenedioxybenzylamine is reacted with 4-(4-chloro-5,6-cyclopenteno-thieno-2,3-d]-pyrimidin-2-yl-benzoic acid methylester yields 4-[4-{3,4-ethylenedioxyphenethylamino)-5,6-cyclopenteno-thieno-[2,3-d]-pyrimidin-2-yl-benzoic acid methylester.

EXAMPLE 393

The reaction procedure as above wherein 3,4-ethylenedioxybenzylamine is reacted with 4-(4-chloro-5,6-cyclohepteno-thieno-[2,3-d]-pyrimidin-2-yl)-benzoic acid methylester yields 4-[4-(3,4-ethylenedioxyphenethylamino)-5,6-cyclohepteno-thieno-[2,3-d]-pyrimidin-2-yl]-benzoic acid methylester.

EXAMPLE 394

The reaction procedure as above wherein 3,4-ethylenedioxybenzylamine is reacted with 4-(4-chloro-6-ethyl-thieno-[2,3-d]-pyrimidin-2-yl)-benzoic acid methylester yields 4-[4-(3,4-ethylenedioxyphenethylamino)-6-ethyl-thieno-[2,3-d]-pyrimidin-2-yl]-benzoic acid methylester.

EXAMPLE 395

The reaction procedure as above wherein 3,4-ethylenedioxybenzylamine is reacted with 4-(4-chloro-6-chloro-thieno-[2,3-d]-pyrimidin-2-yl)-benzoic acid methylester yields 4-[4-(3,4-ethylenedioxyphenethylamino)-6-chloro-thieno-[2,3-d]-pyrimidin-2-yl]-benzoic acid methylester.

EXAMPLE 396

The reaction procedure as above wherein 3,4-ethylenedioxybenzylamine is reacted with 4-(4-chloro-5-chloro-6-methyl-thieno-[2,3-d]-pyrimidin-2-yl)-benzoic acid methylester yields 4-[4-(3,4-ethylenedioxyphenethylamino)-5-chloro-6-methyl-thieno-[2,3-d]-pyrimidin-2-yl]-benzoic acid methylester.

EXAMPLE 397

The reaction procedure as above wherein 3,4-ethylenedioxybenzylamine is reacted with 4-(4-chloro-6-nitro-thieno-[2,3-d]-pyrimidin-2-yl)-benzoic acid methylester yields 4-[4-(3,4-ethylenedioxyphenethylamino)-6-nitro-thieno-[2,3-d]-pyrimidin-2-yl]-benzoic acid methylester.

EXAMPLE 398

The reaction procedure as above wherein 3,4-ethylenedioxybenzylamine is reacted with 4-(4-chloro-5,6-dimethyl-thieno-[2,3-d]-pyrimidin-2-yl)-benzoic acid methylester yields 4-[4-(3,4-ethylenedioxyphenethylamino)-5,6-dimethyl-thieno-[2,3-d]-pyrimidin-2-yl]-benzoic acid methylester.

EXAMPLE 399

The reaction procedure as above wherein 3,4-ethylenedioxybenzylamine is reacted with 4-(4-chloro-6-trifluoromethyl-thieno-[2,3-d]-pyrimidin-2-yl)-benzoic acid methylester yields 4-[4-(3,4-ethylenedioxyphenethylamino)-6-trifluoromethyl-thieno-2,3-d]-pyrimidin-2-yl]-benzoic acid methylester.

EXAMPLE 400

The reaction procedure as above wherein phenethylamine is reacted with 4-(4-chloro-6-methyl-thieno-[2,3-d]-pyrimidin-2-yl)-benzoic acid methylester yields 4-(4-phenethylamino-6-methyl-thieno-[2,3-d]-pyrimidin-2-yl)-benzoic acid methylester;

EXAMPLE 401

The reaction procedure as above wherein phenethylamine is reacted with 4-(4-chloro-5-methyl-thieno-[2,3-d]-pyrimidin-2-yl)-benzoic acid methylester yields 4-(4-phenethylamino-5-methyl-thieno-[2,3-d]-pyrimidin-2-yl)-benzoic acid methylester.

EXAMPLE 402

The reaction procedure as above wherein phenethylamine is reacted with 4-(4-chloro-5,6,7,8-tetrahydro-[1]-benzothieno-[2,3-d]-pyrimidin-2-yl)-benzoic acid methylester yields 4-(4-phenethylamino-5,6-7,8-tetrahydro-[1]-benzothieno-[2,3-d]-pyrimidin-2-yl)-benzoic acid methylester.

EXAMPLE 403

The reaction procedure as above wherein phenethylamine is reacted with 4-(4-chloro-5,6-cyclopenteno-thieno-[2,3-d]-pyrimidin-2-yl)-benzoic acid methylester yields 4-(4-phenethylamino-5,6-cyclopenteno-thieno-[2,3-d]-pyrimidin-2-yl)-benzoic acid methylester.

EXAMPLE 404

The reaction procedure as above wherein phenethylamine is reacted with 4-(4-chloro-5,6-cyclohepteno-thieno-[2,3-d]-pyrimidin-2-yl)-benzoic acid methylester yields 4-(4-phenethylamino-5,6-cyclohepteno-thieno-[2,3-d]-pyrimidin-2-yl) benzoic acid methylester.

EXAMPLE 405

The reaction procedure as above wherein phenethylamine is reacted with 4-(4-chloro-6-ethyl-thieno-[2,3-d]-pyrimidin-2-yl)-benzoic acid methylester yields 4-(4-phenethylamino-6-ethyl-thieno-[2,3-d]-pyrimidin-2-yl)-benzoic acid methylester.

EXAMPLE 406

The reaction procedure as above wherein phenethylamine is reacted with 4-(4-chloro-6-chloro-thieno-[2,3-d]-pyrimidin-2-yl)-benzoic acid methylester yields 4-(4-phenethylamino-6-chloro-thieno-[2,3-d]-pyrimidin-2-yl)-benzoic acid methylester.

EXAMPLE 407

The reaction procedure as above wherein phenethylamine is reacted with 4-(4-chloro-5-chloro-6-methyl-thieno-[2,3-d]-pyrimidin-2-yl)-benzoic acid methylester yields 4-(4-phenethylamino-5-chloro-6-methyl-thieno-[2,3-d]-pyrimidin-2-yl)-benzoic acid methylester.

EXAMPLE 408

The reaction procedure as above wherein phenethylamine is reacted with 4-(4-chloro-6-nitro-thieno-[2,3-d]-pyrimidin-2-yl]-benzoic acid methylester yields 4-(4-phenethylamino-6-nitro-thieno-[2,3-d]-pyrimidin-2-yl)-benzoic acid methylester.

EXAMPLE 409

The reaction procedure as above wherein phenethylamine is reacted with 4-(4-chloro-5,6-dimethyl-thieno-[2,3-d]-pyrimidin-2-yl)-benzoic acid methylester yields 4-(4-phenethylamino-5,6-dimethyl-thieno-[2,3-d]-pyrimidin-2-yl)-benzoic acid methylester.

EXAMPLE 410

The reaction procedure as above wherein phenethylamine is reacted with 4-(4-chloro-6-trifluoromethyl-thieno-[2,3-d]-pyrimidin-2-yl)-benzoic acid methylester yields 4-(4-phenethylamino-6-trifluoromethyl-thieno-[2,3-d]-pyrimidin-yl)-benzoic acid methylester.

EXAMPLE 411

A solution of 4-[4-(3,4-methylenedioxybenzylamino)-6-methyl-thieno-[2,3-d]-pyrimidin-2-yl]-benzoic acid methylester (1.1 g), 2N NaOH (30 ml), and tetrahydrofuran (30 ml) is heated 6hours to 100° C. After cooling and acidifing the solution with 20% HCl, the usual work up yields 4-[4-(3,4-methylenedioxybenzylamino)-6-methyl-thieno-[2,3-d-]pyrimidin-2-yl]-benzoic acid (0.75 g), Mp. >250° C.

EXAMPLES 412–518

Accordingly with the procedure of Example QQ, the following carboxylic acids are obtained from the esters above:

4-[4-(3,4-Methylenedioxybenzyl)-5-methyl-thieno-[2,3-d]-pyrimidin-2-yl]-benzoic acid (Example 412);

4-[4-(3,4-Methylenedioxybenzylamino)-5,6,7,8-tetrahydro-[1]-benzothieno-[2,3-d]-pyrimidin-2-yl]-benzoic acid, dihydrate Mp. 249° C. sodium salt, Mp. 250° C. (Example 413):

4-[4-(3,4-Methylenedioxybenzylamino)-5,6-cyclopenteno-thieno-[2,3-d]-pyrimidin-2-yl]-benzoic acid (Example 414);

4-[4-(3,4-Methylenedioxybenzylamino)-5,6-cyclohepteno-thieno-[2,3-d]-pyrimidin-2-yl]-benzoic acid (Example 415);

4-[4-(3,4-Methylenedioxybenzylamino)-6-ethyl-thieno-[2,3-d]-pyrimidin-2-yl]-benzoic acid, Mp 189° C. (Example 416);

4-4[4-(3,4-Methylenedioxybenzylamino)-6-propyl-thieno-[2,3-d]-pyrimidin-2-yl]-benzoic acid (Example 417);

4-[4-(3,4-Methylenedioxybenzylamino)-6-chloro-thieno-[2,3-d]-pyrimidin-2-yl]-benzoic acid Mp. 250° C. (Example 418);

4-[4-(3,4-Methylenedioxybenzylamino)-5-chgloro-6-methyl-thieno-[2,3-d]-pyrimidin-2yl]-benzoic acid Mp. 250° C. (Example 419);

4-[4-(3,4-Methylenedioxybenzylamino)-6-nitro-thieno-[2,3-d]-pyrimidin-2-yl]-benzoic acid (Example 420);

4-[4(3,4-Methylenedioxybenzylamino)-5,6-dimethyl-thieno-[2,3-d]-pyrimidin-2-yl]-benzoic acid, Mp.172° C. (Example 421);

4-[4-(3,4-Methylenedioxybenzylamino)-6-trifluromethyl-thieno-[2,3-d]-pyrimidin-2-yl]-benzoic acid (Example 422);

4-[4-(3-Chloro-4-methoxybenzylamino)-6-methyl-thieno-[2,3-d]-pyrimidin-2-yl]-benzoic acid (Example 423);

4-[4-(3-Chloro-4-methoxybenzylamino)-5-methyl-thieno-[2,3-d]-pyrimidin-2-yl]-benzoic acid (Example 424);

4-[4-(3-Chloro-4-methoxybenzylamino)-5,6,7,8-tetrahydro-[1]-benzothieno-[2,3-d]-pyrimidin-2-yl]-benzoic acid, Mp. 245° C. (Example 425)

4-[4-(3-Chloro-4-methoxybenzylamino)-5,6-cyclopenteno-thieno-[2,3-d]-pyrimidin-2-yl]-benzoic acid (Example 426);

4-[4-(3-Chloro-4-methoxybenzylamino)-5,6-cyclohepteno-thieno-[2,3-d]-pyrimidin-2-yl]-benzoic acid (Example 427);

4-[4-(3-Chloro-4-methoxybenzylamino)-6-ethyl-thieno-[2,3-d]-pyrimidin-2-yl]-benzoic acid, Mp.257° C. (Example 428);

4-[4-(3-Chloro-4-methoxybenzylamino)-6-chloro-thieno-[2,3-d]-pyrimidin-2-yl]-benzoic acid, Mp. 250° C. (Example 429);

4-[4-(3-Chloro-4-methoxybenzylamino)-5-chloro-6-methyl-thieno-[2,3-d]-pyrimidin2-yl]-benzoic acid, sodium salt, Mp. 250° C. (Example 430);

4-[4-(3-Chloro-4-methoxybenzylamino)-6-nitro-thieno-[2,3-d]-pyrimidin-2-yl]-benzoic acid (Example 431);

4-[4-(3-Chloro-4-methoxybenzylamino)-5,6-dimethyl-thieno-[2,3-d]-pyrimidin-2-yl]-benzoic acid (Example 432);

4-[4-(3-Chloro-4-methoxybenzylamino)-6-trifluoromethyl-thieno-[2,3-d]-pyrimidin-2-yl]-benzoic acid (Example 433);
4-[4-(3,4-Dimethoxybenzylamino)-6-methyl-thieno-[2,3-d]-pyrimidin-2-yl]-benzoic acid (Example 434);
4-[4-(3,4-Dimethoxybenzylamio)-5-methyl-thieno-[2,3-d]-pyrimidin-2-yl]-benzoic acid (Example 435);
4-[4-(3,4-Dimethoxybenzylamino)-5,6,7,8-tetrahydro-[1]-benzothieno-[2,3-d]-pyrimidin-2-yl]-benzoic acid (Example 436);
4-[4-(3,4-Dimethxybenzylamino)-5,6-cyclopenteno-thieno-[2,3-d]-pyrimidin-2-yl]-benzoic acid (Example 437);
4-[4-(3,4-Dimethoxybenzylamino)-5,6-cyclohepteno-thieno-[3,3-d]-pyrimidin-2-yl]-benzoic acid (Example 438);
4-[4-(3,4-Dimethoxybenzylamino)-6-ethyl-thieno-[2,3-d]-pyrimidin-2-yl]-benzoic acid (Example 439);
4-[4-(3,4-Dimethoxybenzylamino)-6-chloro-thieno-[2,3-d]-pyrimidin-2-yl]-benzoic acid (Example 440);
4-[4-(3,4-Dimethoxybenzylamino)-5-chloro-6-methyl-thieno-[2,3-d]-pyrimidin-2-yl]-benzoic acid (Example 441);
4-[4-(3,4-Dimethoxybenzylamino)-6-nitro-thieno-[2,3-d]-pyrimidin-2-yl]-benzoic acid (Example 442);
4-[4-(3,4-Dimethoxybenzylamino)-5,6-dimethyl-thieno-[2,3-d]-pyrimidin-2-yl]-benzoic acid (Example 443);
4-[4-(3,4-Dimethoxybenzylamino)-6-trifluoromethyl-thieno-[2,3-d]-pyrimidin-2-yl]-benzoic acid (Example 444);
4-(4-Benzylamino-6-methyl-thieno-[2,3-d]-pyrimidin-2-yl)-benzoic acid, Mp. 250° C. (Example 445);
4-(4-Benzylamino-5-methyl-thieno-[2,3-d]-pyrimidin-2-yl)-benzoic acid (Example 446);
4-(4-Benzylamino-5,6,7,8-tetrahydro-[1]-benzothieno-[2,3-d]-pyrimidin-2-yl)-benzoic acid, Mp. 270° C. (Example 447);
4-(4-Benzylamino-5,6-cyclopenteno-thieno-[2,3-d]-pyrimidin-2-yl)-benzoic acid (Example 448);
4-(4-Benzylamino)-5,6-cyclohepteno-thieno-[2-,3-d]-pyrimidin-2-yl)-benzoic acid (Example 449);
4-(4-Benzylamino-6-ethyl-thieno-[2,3-d]-pyrimidin-2-yl)-benzoic acid, Mp.172° C. (Example 450);
4-(4-Benzylamino-6-chloro-thieno-[2,3-d]-pyrimidin-2-yl)-benzoic acid (Example 451);
4-(4-Benzylamino-5-chloro-6-methyl-thieno-[2,3-d]-pyrimidin-2-yl)-benzoic acid (Example 452);
4-(4-Benzylamino-6-nitro-thieno-[2,3-d]-pyrimidin-2-yl)-benzoic acid (Example 453);
4-(4-Benzylamino-5,6-dimethyl-thieno-[2,3-d]-pyrimidin-2-yl)-benzoic acid (Example 454);
4-(4-Benzylamino-6-trifluoromethyl-thieno-[2,3-d]-pyrimidin-2-yl)-benzoic acid (Example 455);
4-[4-(4-Fluorobenzylamino)-6-methyl-thieno-[2,3-d]-pyrimidin-2-yl]-benzoic acid (Example 456);
4-[4-(4-Fluorobenzylamino)-5-methyl-thieno-[2,3-d]-pyrimidin-2-yl]-benzoic acid (Example 457);
4-[4-(4-Fluorobenzylamino)-5,6,7,8-tetrahydro-[1]-benzothieno-[2,3-d]-pyrimidin-2-yl]-benzoic acid (Example 458);
4-[4-(4-Fluorobenzylamino)-5,6-cyclopenteno-thieno-[2,3-d]-pyrimidin-2-yl]-benzoic acid (Example 459);
4-[4-(4-Fluorobenzylamino)-5,6-cyclohepteno-thieno-[2,3-d]-pyrimidin-2-yl]-benzoic acid (Example 460);
4-[4-(4-Fluorobenzylamino)-6-ethyl-thieno-[2,3-d]-pyrimidin-2-yl]-benzoic acid (Example 461);
4-[4-(4-Fluorobenzylamino)-6-chloro-thieno-[2,3-d]-pyrimidin-2-yl]-benzoic acid (Example 462);
4-[4-(4-Fluorobenzylamino)-5-chloro-6-methyl-thieno-[2,3-d]-pyrimidin-2-yl]-benzoic acid (Example 463);
4-[4-(4-Fluorobenzylamino)-6-nitro-thieno-[2,3-d]-pyrimidin-2-yl]-benzoic acid (Example 464);
4-[4-(4-Fluorobenzylamino)-5,6-dimethyl-thieno-[2,3-d]-pyrimidin-2-yl]-benzoic acid (Example 465);
4-[4-(4-Fluorobenzylamino)-6-trifluoromethyl-thieno-[2,3-d]-pyrimidin-2-yl]-benzoic acid (Example 466);
4-[4-(3,4-Dichlorobenzylamino)-6-methyl-thieno-[2,3-d]-pyrimidin-2-yl]-benzoic acid (Example 467);
4-[4-(3,4-Dichlorobenzylamino)-5-methyl-thieno-[2,3-d]-pyrimidin-2-yl]-benzoic acid (Example 468);
4-[4-(3,4-Dichlorobenzylamino)-5,6,7,8-tetrahydro-[1]-benzothieno-[2,3-d]-pyrimidin-2yl]-benzoic acid (Example 469);
4-[4-(3,4-Dichlorobenzylamino)-5,6-cyclopenteno-thieno-[2,3-d]-pyrimidin-2-yl]-benzoic acid (Example 470);
4-[4-(3,4-Dichlorobenzylamino)-5,6-cyclohepteno-thieno-[2,3-d]-pyrimidin-2-yl]-benzoic acid (Example 471);
4-[4-(3,4-Dichlorobenzylamino)-6-ethyl-thieno-[2,3-d]-pyrimidin-2-yl]-benzoic acid (Example 472);
4-[4-(3,4-Dichlorobenzylamino)-6-chloro-thieno-[2,3-d]-pyrimidin-2-yl]-benzoic acid (Example 473);
4-[4-(3,4-Dichlorobenzylamino)-5-chloro-6-methyl-thieno-[2,3-d]-pyrimidin-2-yl]-benzoic acid (Example 474);
4-[4-(3,4-Dichlorobenzylamino)-6-nitro-thieno-[2,3-d]-pyrimidin-2-yl]-benzoic acid (Example 475);
4-[4-(3,4-Dichlorobenzylamino)-5,6-dimethyl-thieno-[2,3-d]-pyrimidin-2-yl]-benzoic acid (Example 476);
4-[4-(3,4-Dichlorobenzylamino)-6-trifluoromethyl-thieno-[2,3-d]-pyrimidin-2-yl]-benzoic acid (Example 477);
4-[4-(3-Nitrobenzylamino)-6-methyl-thieno-[2,3-d]-pyrimidin-2-yl]-benzoic acid (Example 478);
4-[4-(3-Nitrobenzylamino)-5-methyl-thieno-[2,3-d]-pyrimidin-2-yl]-benzoic acid (Example 479);
4-[4-(3-Nitrobenzylamino)-5,6,7,8-tetrahydro-[1]-benzothieno-[2,3-d]-pyrimidin-2-yl]-benzoic acid (Example 480);
4-[4-(3-Nitrobenzylamino)-5,6-cyclopenteno-thieno-[2,3-d]-pyrimidin-2-yl]-benzoic acid (Example 481);
4-[4-(3-Nitrobenzylamino)-5,6-cyclohepteno-thieno-[2,3-d]-pyrimidin-2-yl]-benzoic acid (Example 482);
4-[4-(3-Nitrobenzylamino)-6-ethyl-thieno-[2,3-d]-pyrimidin-2-yl]-benzoic acid (Example 483);
4-[4-(3-Nitrobenzylamino)-6-chloro-thieno-[2,3-d]-pyrimidin-2yl]-benzoic acid (Example 484);
4-[4-(3-Nitrobenzylamino)-5-chloro-6-methyl-thieno-[2,3-d]-pyrimidin-2-yl]-benzoic acid (Example 485);
4-[4-(3-Nitrobenzylamino)-6-nitro-thieno-[2,3-d]-pyrimidin-2-yl]-benzoic acid (Example 486);
4-[4-(3,4-Nitrobenzylamino)-5,6-dimethyl-thieno-[2,3-d]-pyrimidin-2-yl]-benzoic acid (Example 487);
4-[4-(3-Nitrobenzylamino)-6-trifluoromethyl-thieno-[2,3-d]-pyrimidin-2-yl]-benzoic acid (Example 488);
4-[4-(3,4-Methylenedioxyphenethylamino)-6-methyl-thieno-[2,3-d]-pyrimidin-2-yl]-benzoic acid (Example 489);
4-[4-(3,4-Methylenedioxyphenethylamino)-5-methyl-thieno-[2,3-d]-pyrimidin-2-yl]-benzoic acid (Example 490);
4-[4-(3,4-Methylenedioxyphenethylamino)-5,6,7,8-tetrahydro-[1]-benzothieno-[2,3-d]-pyrimidin-2-yl]-benzoic acid (Example 491);
4-[4-(3,4-Methylenedioxyphenethylamino)-5,6-cyclopenteno-thieno-[2,3-d]-pyrimidin-2-yl]-benzoic acid (Example 492);
4-[4-(3,4-Metylenedioxyphenethylamino)-6-ethyl-thieno-[2,3-d]-pyrimidin-2-yl]-benzoic acid (Example 493);

4-[4-(3,4-Methylenedioxyphenethylamino)-6-chloro-thieno-[2,3-d]-pyrimidin-2-yl]-benzoic acid (Example 494);

4-[4-(3,4-Methylenedioxyphenethylamino)-5-chloro-6-methyl-thieno-[2,3-d]-pyrimidin-2-yl]-benzoic acid (Example 495);

4-[4-(3,4-Methylenedioxyphenethylamino)-6-nitro-thieno-[2,3-d]-pyrimidin-2-yl]-benzoic acid (Example 496);

4-[4-(3,4-Methylenedioxyphenethylamino)-5,6-dimethyl-thieno-[2,3-d]-yrimidin-2-yl]-benzoic acid (Example 497);

4-[-4-(3,4-Methylenedioxyphenethylamino)-6-trifluoromethyl-thieno-[2,3-d]-pyrimidin-2-yl]-benzoic acid (Example 498);

4-[4-(3,4-Ethylenedioxyphenethylamino)-6-methyl-thieno-[2,3-d]-pyrimidin-2-yl]-benzoic acid (Example 499);

4-[4-(3,4-Ethylenedioxyphenethylamino)-5-methyl-thieno-[2,3-d]-pyrimidin-2-yl]-benzoic acid (Example 500);

4-[4-(3,4-Ethylenedioxyphenethylamino)-5,6,7,8-tetrahydro-[1]-benzothieno-[2,3-d]-pyrimidin-2-yl]-benzoic acid (Example 501);

4-[4-(3,4-Ethylenedioxyphenethylamino)-5,6-cyclopenteno-thieno-[2,3-d]-pyrimidin-2-yl]-benzoic acid (Example 501A);

4-[4-(3,4-Ethylenedioxyphenethylamino)-6-ethyl-thieno-[2,3-d]-pyrimidin-2-yl]-benzoic acid (Example 502);

4-[4-(3,4-Ethylenedioxyphenethylamino)-6-chloro-thieno-[2,3-d]-pyrimidin-2-yl]-benzoic acid (Example 503);

4-[4-(3,4-Ethylenedioxyphenethylamino)-5-chloro-6-methyl-thieno-[2,3-d]-pyrimidin-2-2yl]-benzoic acid (Example 504);

4-[4-(3,4-Ethylenedioxyphenethylamino)-6-nitro-thieno-[2,3-d]-pyrimidin-2-yl]-benzoic acid (Example 505);

4-[4-(3,4-Ethylenedioxyphenethylamino)-5,6-dimethyl-thieno-[2,3-d]-pyrimidin-2-yl]-benzoic acid (Example 506);

4-[4-(3,4-Ethylenedioxyphenethylamino)-6-trifluoromethyl-thieno-[2,3-d]-pyrimidin-2-yl]-benzoic acid (Example 507);

4-(4-Phenethylamino-6-methyl-thieno-[2,3-d]-pyrimidin-[2-yl]-benzoic acid (Example 508);

4-(4-Phenethylamino-5-methyl-thieno-[2,3-d]-pyrimidin-2-yl)-benzoic acid (Example 509);

4-(4-Phenethylamino-5,6,7,8-tetrahydro-[1]-benzothieno-[2,3-d]-pyrimidin-2-yl)-benzoic acid (Example 510);

4-(4-Phenethylamino-5,6-cyclopenteno-thieno-[2,3-d]-pyrimidin-2-yl)-benzoic acid (Example 511);

4-(4-Phenethylamino-5,6-cyclohepteno-thieno-[2,3-d]-pyrimidin-2yl)-benzoic acid (Example 512);

4-(4-Phenethylamino-6-ethyl-thieno-[2,3-d]-pyrimidin-2-yl)-benzoic acid (Example 513);

4-(4-Phenethylamino-6-chloro-thieno-[2,3-d]-pyrimidin-2-yl)-benzoic acid (Example 514);

4-(4-Phenetylamino-5-chloro-6-methyl-thieno-[2,3-d]-pyrimidin-2-yl)-benzoic acid (Example 515);

4-(4-Phenethylamino-6-nitro-thieno-[2,3-d]-pyrimidin-2-yl)-benzoic acid (Example 516);

4-(4-Phenethylamino-5,6-dimethyl-thieno-[2,3-d]-pyrimidin-2-yl)-benzoic acid (Example 517);

4-(4-Phenethylamino-6-trifluoromethyl-thieno-[2,3-d]-pyrimidin-2-yl)-benzoic acid (Example 518);

EXAMPLE 519

According to example 5, 3-[4-(3,4-Methylenedioxybenzylamino)-5,6,7,8-tetrahydro-[1]-benzothieno-[2,3-d]-pyrimidin-2-yl]-benzoic acid is obtained using 3-cyanobenzoic acid methylester and subsequent hydrolysis.

EXAMPLES 520–630

In analogy to examples 5 and 6 the following carboxylic acids are obtained using 4-cyanocylohexancarbonic acid ester:

4-[4-(3,4-Methylenedioxybenzylamino)-6-methyl-thieno-[2,3-d]-pyrimidin-2-yl]-cyclohexancarboxylic acid (Example 520);

4-[4-(3,4-Methylenedioxybenzylamino)-5-methyl-thieno-[2,3-d]-pyrimidin-2-yl]-cyclohexancarboxylic acid (Example 521);

4-[4-(3,4-Methylenedioxybenzylamino)-5,6,7,8-tetrahydro-[1]-benzothieno-[2,3-d]-pyrimidin-2-yl]-cyclohexancarboxylic acid (Example 522);

4-[4-(3,4-Methylenedioxybenzylamino)-5,6-cyclopenteno-thieno-[2,3-d]-pyrimidin-2-yl]-cyclohexancarboxylic acid (Example 523);

4-[4-(3,4-Methylenedioxybenzylamino)-5,6-cyclohepteno-thieno-[2,3-d]-pyrimidin-2-2yl]-cyclohexancarboxylic acid (Example 524);

4-[4-(3,4-Methylenedioxybenzylamino)-6-ethyl-thieno-[2,3-d]-pyrimidin-2-yl]-cyclohexancarboxylic acid (Example 525);

4-[4-(3,4-Methylenedioxybenzylamino)-6-chloro-thieno-[2,3-d]-p din-2-yl]-cyclohexancorboxylic acid (Example 526);

4-[4-(3,4-Methylenedioxybenzylamino)-5-chloro-6-methyl-thieno-[2,3-d]-pyrimidin-2-yl]-cyclohexancarboxylic acid (Example 527);

4-[4-(3,4-Mehylenedioxybenzylamino)-6-nitro-thieno-[2,3-d]-pyrimidin-2-yl]-cyclohexancarboxylic acid (Example 528);

4-[4-(3,4-Methylenedioxybenzylamino)-5,6-dimethyl-thieno-[2,3-d]-pyrimidin-2-yl]-cyclohexancarboxylic acid (Example 529);

4-[4-(3,4-Methylanedioxybenzylamino)-6-trifluoromethyl-thieno-[2,3-d]-pyrimidin-2-yl]-cylohexancarboxylic acid (Example 530);

4-[4-(3-chloro-4-methoxybenzylamino)-6-methyl-thieno-[2,3-d]-pyrimidin-2-yl]-cyclohexancarboxylic acid (Example 531);

4-[4-(3-chloro-4-methoxybenzylamino)-5-methyl-thieno[2,3-d]-pyrimidin-2-yl]-cyclohexancarboxylic acid (Example 532);

4-[4-(3-Chloro-4-methoxybenzylamino)-5.6.7.8-tetrahydro-[1]-benzothieno-[2,3-d]-pyrimidin-cyclohexancarboxylic acid, amorphous (Example 533);

4-[4-(3-Chloro-4-methoxybenzylamino)-5,6-cyclopenteno-thieno-[2,3-d]-pyrimidin-2-yl]-cyclohexancarboxylic acid (Example 534);

4-[4-(3-Chloro-4-methoxybenzylamino)-5,6-cycloheptneno-thieno-[2,3]-pyrimidin-2-yl]-cyclohexancarboxylic acid (Example 535);

4-[4-(3-Chloro-4-methoxybenzylamino)-6-ethyl-thieno-[2,3-d]-pyrimidin-2-yl]-cyclohexancarboxylic acid (Example 536);

4-[4-(3-Chloro-4-methoxybenzylamino)-6-chloro-thieno-[2,3-d]-pyrimidin-2-yl]-cyclohexancarboxylid acid (Example 537);

4-[4-(3-Chloro-4-methoxybenzylamino)-5-chloro-6-methyl-thieno[2,3-d]pyrimidin-2-yl]-cyclohexancarboxylic acid (Example 538);

4-[4-(3-Chloro-4-methoxybenzylamino)-6-nitro-thieno-[2,3-d]-pyrimidin-2-yl]-cyclohexancarboxylic acid (Example 539);

4-[4-(3-Chloro-4-methoxybenzylamino)-5,6-dimethyl-thieno-[2,3-d]-pyrimidin-2-yl]-cyclohexancarboxylic acid (Example 540);

4-[4-(3-Chloro-4-methoxybenzylamino)-6-trifluoromethyl-thieno-[2,3-d]-pyrimidin-2-yl]-cyclohexancarboxylic acid (Example 541);

4-[4-(3,4-Dimethoxybenzylamino)-6-methyl-thien0-[2,3-d]-pyrimidin-2-yl]-cyclohexancaboxylid acid (Example 542);

4-[4-(3,4-Dimethoxybenzylamino)-5-methyl-thieno-[2,3-d]-pyrimidin-2-y;]-cyclohexancarboxylic acid (Example 543);

4-[4-(3,4-Dimethoxybenzylamino)-5,6,7,8-tetrahydro-[l1]-benzothieno-[2,3-d]-pyrimidin-2-yl-]-cyclohexancarboxylic acid (Example 544);

4-[4-(3,4-Dimethoxybenzylamino)-5,6-cyclopenteno-thieno-[2,3-d]-pyrimidin-2-yl]-cyclohexancarboxylic acid (Example 545);

4-[4-(3,4-Dimethoxybenzylamino)-5,6-cyclohepteno-thieno-[2,3-d]-pyrimidin-2-yl]-cyclohexancarboxylic acid (Example 546);

4-[4-(3,4-Dimethoxybenzylamino)-6-ethyl-thieno-[2,3-d]-pyrimidin-2-yl]-cyclohexancarboxylic acid (Example 547);

4-[4-(3,4-Dimethoxybenzylamino)-6-chloro-thieno-[2,3-d]-pyrimidin-2-yl]-cyclohexancarboxylic acid (Example 548);

4-[4-(3,4-Dimethoxybenzylamino)-5-chloro-6-methyl-thieno-[2,3-d]-pyrimidin-2-yl]-cyclohexancarboxylic acid (Example 549);

4-[4-(3,4-Dimethoxybenzylamino)-nitro-thieno-[2,3-d]-pyrimidin-2-yl]-cyclohexancarboxylic acid (Example 550)

4-[4-(3,4-Dimethoxybenzylamino)-5,6-dimethyl-thieno-[2,3-d]-pyrimidin-2-yl]-cyclohexancarboxylic acid (Example 551);

4-[4-(3,4-Dimethoxybenzylamino)-6-trifluoromethyl-thieno-[2,3-d]-pyrimidin-2-yl]-cyclohexancarboxylic acid (Example 552);

4-(4-Benzylamino-6-methyl-thieno-[2,3-d]-pyrimidin-2-yl)-cyclohexancarboxylic acid (Example 553);

4(4-Benzylamino-5-methyl-thieno-[2,3-d]-pyrimidin-2-yl)-cyclohexancarboxylic acid (Example 554);

4-(4-Benzylamino-5,6-cyclopenteno-thieno-[2,3-d]-pyrimidin-2-yl)-cyclohexancarboxylic acid (Example 555);

4-(4-Benzylamino)-5,6-cyclohepteno-thieno-[2,3-d]-pyrimidin-2-yl)-cyclohexancarboxylic acid (Example 556);

4-(4-Benzylamino-6-ethyl-thieno-[2,3-d]-pyrimidin-2-yl)-cyclohexancarboxylic acid (Example 557);

4-(4-Benzylamino-6-chloro-thieno-[2,3-d]-pyrimidin-2-yl)-cyclohexancarboxylic acid (Example 558);

4-(4-Benzylamino-5-chloro-6-methyl-thieno-[2,3-d]-pyrimidin-2-yl)-cyclohexancarboxylic acid (Example 559);

4-(4-Benzylamino-6-nitro-thieno-[2,3-d]-pyrimidin-2yl)-cyclohexancarboxylic acid (Example 560);

4-(4-Benzylamino-5,6-dimethyl-thieno-[2,3-d]-pyrimidin-2-yl)-cyclohexancarboxylic acid (Example 561);

4-(4-Benzylamino-6-trifluoromethyl-thieno-[2,3-d]-pyrimidin-2-yl)-cyclohexancarboxylic acid (Example 562);

4-[4-(4-Fluorobenzylamino)-6methyl-thieno-[2,3-d]-pyrimidin-2-yl]-cyclohexancarboxylic acid (Example 563);

4-[4-(4-Fluorobenzylamino)-5-methyl-thieno-[2,3-d]-pyrimidin-2-yl]-cyclohexancarboxylic acid (Example 564);

4-[4-(4-fluorobenzylamino)-5,6,7,8-tetrahydro-[1]-benzothieno-[2,3-d]-pyrimidin-2-yl]-cyclohexancarboxylic acid (Example 565);

4-[4-(4Fluorobenzylamino)-5,6-cyclopenteno-thieno-[2,3-d]-pyrimidin-2-yl]-cyclohexancarboxylic acid (Example 567);

4-[4-(4-Fluorobenzylamino)-5,6-cyclohepteno-thieno-[2,3-d]-pyrimdin-2-yl]-cyclohexancarboxylic acid (Example 568);

4-[4-(4-Fluorobenzylamino)-6-ethyl-thieno-[2,3-d]-pyrimidin-2-yl-]-cyclohexancarboxylic acid (Example 569);

4-[4-(4-Fluorobenzylamino)-6-chloro-thieno-[2,3-d]-pyrimidin-2-yl]-cyclohexancarboxylic acid (Example 570);

4-[4-(4-Fluorobenzylamino)-5-chloro-6-methyl-thieno-[2,3-d]-pyrimidin-2-yl]-cyclohexancarboxylic acid (Example 571);

4-[4-(4-Fluorobenzylamino)-6-nitro-thieno-[2,3-d]-pyrimidin-2-yl]-cyclohexancarboxylic acid (Example 572);

4-[4-(4-Fluorobenzylamino)-5,6-dimethyl-thieno-[2,3-d]-pyrimidin-2-yl]-cyclohexancarboxylic acid (Example 573);

4-[4-(-Fluorobenzylamino)-6-trifluoromethyl-thieno-[2,3-d]-pyrimidin-2-yl]-cyclohexancarboxylic acid (Example 574);

4-[4-(4-Dichlorobenzylamino)-6-methyl-thieno-[2,3-d]-pyrimidni-2-yl]-cyclohexancarboxylic acid (Example 575);

4-[4-(3,4-Dichlorobenzylamino)-5-methyl-thieno-[2,3-d]-pyrimidin-2-yl]-cyclohexancarbonic acid (Example 576);

4-[4-(3,4-Dichlorobenzyalmino)-5,6,7,8-tetrahydro-[1]-benzothieno-[2,3-d]-pyrimidin-2-yl]-cyclohexancarboxylic acid (Example 577);

4-[4-(3,4-Dichlorobenzylamino)-5,6-cyclopenteno-thieno-[2,3-d]-pyrimidin-2-yl]-cyclohexancarboxylic acid (Example 578);

4-[4-(3,4-Dichlorobenzylamino)-5,6-cyclohepteno-thieno-[2,3-d]-pyrimidin-2-yl]-cyclohexancarboxylic acid (Example 579);

4-[4-(3,4-Dichlorobenzylamino)-6-ethyl-thieno-[2,3-d]-pyrimidin-2-yl]-cyclohexancarboxylic acid (Example 580);

4-[4-(3,4-Dichlorobenzylamino)-6-chloro-thieno-[2,3-d]-pyrimidin-2-yl]-cyclohexancarboxylic acid (Example 581);

4-4[4-(3,4-Dichlorobenzylamino)-5-chloro-6-methyl-thieno-[2,3-d]-pyrimidin-2-yl]-cyclohexancarboxylic acid (Example 582);

4-[4-(3,4-Dichlorobenzylamino)-6-nitro-thieno-[2,3-d]-pyrimidin-2-yl]-cyclohexancarboxylic acid (Example 583);

4-[4-(3,4-Dichlorobenzylamino)-5,6-dimethyl-thieno-[2,3-d]-pyrimidin-2-yl]-cyclohexancarboxylic acid (Example 584);

4-[4-(3,4-Dichlorobenzylamino)-6-trifluoromethyl-thieno-[2,3-d]-pyrimidin-2yl]-cyclohexancarboxylic acid (Example 585);

4-[4-(3-Nitrobenzylamino)-6-methyl-thieno-[2,3-d]-pyrimidin-2yl]-cyclohexancarboxylic acid (Example 586);

4-[4-(3-Nitrobenzylamino)-5-methyl-thieno-[2,3-d]-pyrimidin-2-yl]-cyclohexancarboxylic acid (Example 587);

4-[4-(3-Nitrobenzylamino)-5,6,7,8-tetrahydro-[1]-benzothieno-[2,3-d]-pyrimidin-2-yl]-cyclohexancarboxylic acid (Example 588);

4-[4-(3-Nitrobenzylamino)5,6-cyclopenteno-thieno-[2,3-d]-pyrimidin-2-yl]-cyclohexancarboxylic acid (Example 589);

4-[4-(3-Nitrobenzylamino)-5,6-cyclohepteno-thieno-[2,3-d]-pyrimidin-2-yl]-cyclohexancarboxylic acid (Example 590);

4-[4-(3-Nitrobenzylamino)-6-ethyl-thieno-[2,3-d]-pyrimidin-2-yl]-cyclohexancarboxylic acid (Example 591);

4-[4-(3-Nitrobenzylamino)-6-chloro-thieno-[2,3-d]-pyrimidin-2-yl]-cyclohexancarboxylic acid (Example 592);

4-[4-(3-Nitrobenzylamino)-5-chloro-6-methyl-thieno-[2,3-d]-pyrimidin-2-yl]-cyclohexancarboxylic acid (Example 593);

4-[4-(3-Nitrobenzylamino)-6-nitro-thieno-[2,3-d]-pyrimidin-2-yl]-cyclohexancarboxylic acid (Example 594);

4-[4-(3-Nitrobenzylamino)-5,6-dimethyl-thieno-[2,3-d]-pyrimidin-2-yl]-cyclohexancarboxylic acid (Example 595);

4-[4-(3-Nitrobenzylamino)-6-trifluoromethyl-thieno-[2,3-d]-pyrimidin-2-yl]-cyclohexancarboxylic acid (Example 596);

4-[4-(3,4-Methylenedioxyphenethylamino)-6-methyl-thieno-[2,3-d]-pyrimidin-2-yl]-cyclohexancarboxylic acid (Example 597);

4-[4-(3,4-Methylenedioxyphenethylamino)-5-methyl-thieno-[2,3-d]-p din-2-yl]-cyclohexancarboxylic acid (Example 598);

4-[4-(3,4-Methylnedioxyphenethylamino)-5,6,7,8-tetrahydro-[1]-benzothieno-[2,3-d]-pyrimidin-2-yl]-cyclohexancarboxylic acid (Example 599);

4-[4-(3,4-Methylenedioxyphenethylamino)-5,6-cyclopenteno-thieno-[2,3-d]-pyrimidin-2-yl]-cyclohexancarboxylic acid (Example 600);

4-[4-(3,4-Methylenedioxyphenethylamino)-5,6-cyclohepteno-thieno-[2,3-d]-pyrimidin-2-yl]-cyclohexancaroboxylic acid (Example 601);

4-[4-(3,4-Methylenedioxyphenethylamino)-6-ethyl-thieno-[2,3-d]-pyrimidin-3-yl]-cyclohexancarboxylic acid (Example 602);

4-[4-(3,4-Methylenedioxyphenethylamino)-6-chloro-thieno-[2,3-d]-pyrimidin-2-yl]-cyclohexancarboxylic acid (Example 603);

4-[4-(3,4-Methylenedioxyphenethylamino)-6-chloro-thieno-[2,3-d]-pyrimidin-2-yl]-cyclohexancarboxylic acid (Example 604);

4-[4-(3,4-Methylenedioxyphenethylamino)-5-chloro-6-methyl-thieno-[2,3-d]-pyrimidin-2-yl]-cyclohexancarboxylic acid (Example 605);

4-[4-(3,4-Methylenedioxyphenethylamino)-6-nitro-thieno-[2,3-d]-pyrimidin-2-yl]-cyclohexancarboxylic acid (Example 606);

4-[4-(3,4-Methylenedioxyphenethylamino)-5,6-dimethyl-thieno-[2,3-d]-pyrimdin-2-yl]-cyclohexancarboxylic acid (Example 607);

4-[4-(3,4-Methylenedioxyphenethylamino)-6-trifluoromethyl-thieno-[2,3-d]-pyrimdin-2-yl]-cyclohexancarboxylic acid (Example 608);

4-[4-(3,4-Ethylenedioxyphenethylamino)-6-methyl-thieno-[2,3-pyrimidin-2-yl]-cyclohexancarboxyclic acid (Example 609);

4-[4-(3,4-Ethylenedioxyphenelamino)-5-methyl-thieno-[2,3-d]-p din-[2-yl]-cyclohexancarboxylic acid (Example 610);

4-[4-(3,4-Ethylenedioxyphenelamino)-5,6,7,8-tetrahydro-[1]-benzothieno-[2,3-d]-pyrimidin-2-yl]-cyclohexancarboxylic acid (Example 611);

4-[4-(3,4-Ethylenedioxyphenlamino)-5,6-cyclopenteno-thieno-[2,3-d]-pyrimidin-2-yl]-cyclohexancarbonic acid (Example 612);

4-[4-(3,4-Ethylenedioxyphenelamino)-5,6-cyclohepteno-thieno- {2,3-d]-pyrimidin-2-yl]-cyclohexancarboxylic acid (Example 613);

4-[4-(3,4-Ethylenedioxyphenelamino)-6-ethyl-thieno-[2,3-d]-pyrimidin-2-yl]-cyclohexancarboxylic acid (Example 614);

4-[4-(3,4-Ethylenedioxyphenelamino)-6-chloro-thieno-[2,3-d]-pyrimidin-2-yl]-cyclohexhancarboxylic acid (Example 615);

4-[4-(3,4-Ethylenedioxyphenelamino)-5-chloro-6-methyl-thieno-[2,3-d]-pyrimidin-2-yl]-cyclohexancarboxylic acid (Example 616);

4-[4-(3,4-Ethylenedioxyphenelamino)-6-nitro-thieno-[2,3-d]-pyrimidin-2-yl]-cyclohexancarboxylic acid (Example 617);

4-[4-(3,4-Ethylenedioxyphenethylamino)-5,6-dimethyl-thieno-[2,3-d]-pyrimidin-2-yl]-cyclohexancarboxylic acid (Example 618);

4-[4-(3,4-Ethylenedioxyphenethylamino)-6-trifluoromethyl-thieno-[2,3-d]-pyrimidin-2-yl]-cyclohexancarboxylic acid (Example 619);

4-(4-Phenethylamino-6-methyl-thieno-[2,3-d]-pyrimidin-2-yl)-cyclohexancarboxylic acid (Example 620);

4-(4-Phenethylamino-5-methyl-thieno-[2,3-d]-pyrimidin-2-yl)-cyclohexancarboxylic acid (Example 621);

4-(4-Phenethylamino-5,6,7,8-tetrahydro-[1]-benzothieno-[2,3]-pyrimidin-2-yl)-cyclohexancarboxylic acid (Example 622);

4-(4-Phenethylamino-5,6-cyclopenteno-thieno-[2,3-d]-pyrimidin-2-yl)-cyclohexancarboxylic acid (Example 623);

4-(4-phenethylamino-5,6-cyclohepteno-thieno-[2,3-d]-pyrimidin-2-yl)-cyclohexancarboxylic acid (Example 624);

4-(4-Phenethylamino-6-ethyl-thieno-[2,3-d]-pyrimidin-2-yl)-cyclohexancarboxylic acid (Example 625);

4-(4-Phenethylamino-6-chloro-thieno-[2,3-d]-pyrimidin-2-yl)-cyclohexancarboxylic acid (Example 626);

4-(4-Phenethylamino-5-chloro-6-methyl-thieno-[2,3-d]-pyrimidin-2-yl)-cyclohexancarboxylic acids (Example 627);

4-(4-Phenethylamino-6-nitro-thieno-[2,3-d]-pyrimidin-2-yl)-cyclohexancarboxylic acid (Example 628);

4-(4-Phenethylamino-5,6-dimthyl-thieno-[2,3-d]-pyrimidin-2-yl)-cyclohexancarboxylic acid (Example 629);

4-(4-Phenethylamino-6-trifluoromethyl-thieno-[2,3-d]-pyrimidin-2-yl)-cyclohexancarboxylic acid (Example 630);

EXAMPLE 631

A solution of 4-[4-(3-nitrobenzylamino)-5-methyl-thieno-[2,3-d]-pyrimidn-2-yl]-benzoic acid in methanol is hydrogenated in the presence of Raney-Nickel. The catalyst is filtered off, and the solution is concentrated. Recrystallisation yields 4-[4-(3-aminobenzylamino)-5-methyl-thieno-[2,3-d]-pyrimidin-2-yl]-benzoic acid.

EXAMPLE 632

A solution of 4-[4-(3-aminobenzylamino)-5-methyl-thieno-[2,3-d]-pyrimidin-2-yl]-benzoic acid (6 g) and titanium tetrachloride (0.5 g) in methanol (100 ml) is charged with freshly distilled acetaldehyde (1 ml). Sodium cyanoborohydride (4 g) is added, and the mixture is stirred 30 hours. Addition of semiconcentrated HCl and the usual workup yields 4-[4-(3-N-ethylaminobenzylamino)-5-methyl-thieno-[2,3-d]-pyrimidin-2-yl]-benzoic acid.

EXAMPLE 633

In analogy to example 2, the reaction of 2-chloro-5,6,7,8-tetrahydro-4-(3,4-methylenedioxybenzylamino)-[1]-benzothieno-[2,3-d]-pyrimidine with piperazin-1-yl-ethylacetate yields {4-[4-(3,4-methylenedioxybenzylamino)-5,6,7,8-tetrahydro-[1]-benzothieno-[2,3-d]-pyrimidin-2-yl]-piperazin-yl}-ethyl acetate. Ester hydrolysis gives {4-[4-(3,4-methylenedioxybenzylamino)-5,6,7,8-tetrahydro-[1]-benzothieno-[2,3-d]-pyrimidin-2-yl]-piperizin-1-yl}-acetic acid, Mp250° C. (decomp.).

EXAMPLE 634

In analogy to example 2, the reaction of 2-chloro-5,6,7,8-tetrahydro-4-(3,4-methylenedioxybenzylamino)-[1]-benzothieno-[2,3-d]-pyrimidine with piperidin-4-yl ethyl acetate yields {1-[4-(3,4-methylenedioxybenzylamino)-5,6,7,8-tetrahydro-[1]-benzothieno-[2,3-d]-pyrimidin-2-yl]-piperidinyl-4-yl}ethyl acetate Ester hydrolysis gives { 1-[4-(3,4-methylenedioxybenzylamino)-5,6,7,8-tetrahydro-[1]-benzothieno-[2,3-d]-pyrimidin-2-yl]-piperidinyl-4-yl} acetic acid, amorphous

EXAMPLE 635

In analogy to examples 4 and 5, {4-[4-(3,4-methylenedioxybenzylamino)-5,6,7,8-tetrahydro-[1]-benzothieno-[2,3-d]-pyrimidin-2-yl]-phenyl}-ethylacetate is obtained. Ester hydrolysis gives {4-[4-(3,4-methyledioxybenzylamino)-5,6,7,8-tetrahydro-[1]-benzothieno-[2,3-d]-pyrimidin-2-yl]-phenyl}-acetic acid, Mp 214° C.

EXAMPLE 636

In analogy to examples 4 and 5, {4-[4-(3-chloro-4-methoxybenzylamino)-5,6,7,8-tetrahydro-[1]-benzothieno-[2,3-d]-pyrimidin-2-yl]phenyl}ethylacetate. Ester hydrolysis yields {4-[4-{3-chloro-4-methoxybenzylamino)-5,6,7,8-tetrahydro-[1]-benzothieno-[2,3-d]-pyrimdin-2-yl]-phenyl}-acetic acid, sodium salt, Mp 250° C.

We claim:

1. A method for inhibiting the growth of neoplastic cells comprising exposing the cells to a growth inhibiting effective amount of a compound of Formula I:

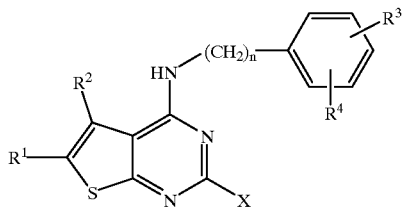

(I)

wherein $R_1$ and $R_2$ are independently selected from the group consisting of hydrogen, A, OA, alkenyl, alkynyl, $-NO_2$, $-CF_3$ or halogen, with the proviso that one of $R_1$ or $R_2$ is not hydrogen; or $R_1$ and $R_2$ together form a $C_{3-5}$ alkylene group;

$R_3$ and $R_4$ are independently selected from the group consisting of hydrogen, A, $-OA$, halogen, $-NO_2$, $-NH_2$, $-NHA$ or $-NAA'$, or $R_3$ and $R_4$ are together form a moiety selected from the group consisting of $-O-CH_2-CH_2-$, $-O-CH_2-O-$ or $-O-CH_2-CH_2-O$, X is selected from the group consisting of a substituted 5–7 membered saturated heterocyclic ring or a substituted saturated or saturated isocyclic ring, wherein the substitutents on the "X" ring are one or two selected from the group consisting of $-COOH$, $-COOA$, $-CONH_2$, $-CONAA'$, $-CONHA$, $-CN$, $-CH_2COOH$ or $-CH_2CH_2COOH$;

A and A' are independently selected from the group consisting of hydrogen or $C_{1-6}$ alkyl; and n is 0, 1, 2 or 3; and physiologically acceptable salts thereof.

2. The method of claim 1 wherein X is single or double substituted phenyl, 1-piperidinyl or cyclohexyl wherein said substitutents are selected from the group consisting of $-COOH$, $-COOA$, $-CONH_2$, $-CONAA'$, $-CONHA$, $-CN$, $-CH_2COOH$ or $-CH_2CH_2COOH$.

3. The method of claim 2 wherein $R_1$ and $R_2$ are independently selected from the group consisting of hydrogen, A, OA, $NO_2$, $CF_3$ or halogen, with the proviso that one of $R_1$ and $R_2$ is not hydrogen; $R_3$ and $R_4$ together form a moiety selected from the group consisting of $-O-CH_2-CH_2-$, $-O-CH_2-O-$ or $-O-CH_2-CH_2-O$; and n is 1.

4. The method of claim 2 wherein $R_3$ and $R_4$ are independently selected from the group consisting of hydrogen, A, OA, halogen, $-NO_2$, $-NH_2$, $-NHA$ or $-NAA'$; and n is 1.

5. The method of claim 2 wherein $R_1$ and $R_2$ together form a $C_{3-5}$ alkylene; $R_3$ and $R_4$ together form a moiety selected from the group consisting of $-O-CH_2-CH_2-$, $-O$, $-CH_2-O-$ or $-O-CH_2-CH_2-O$; and n is 1.

6. The method of claim 2 wherein $R_1$ and $R_2$ together form a $C_{3-5}$ alkylene; $R_3$ and $R_4$ are independently selected from the group consisting of hydrogen, A, OA, halogen, $NO_2$, $NH_2$, NHA or NAA'; and n is 1.

7. A method of treating a mammal having precancerous lesions comprising administering a pharmacologically effective amount of a compound of Formula I:

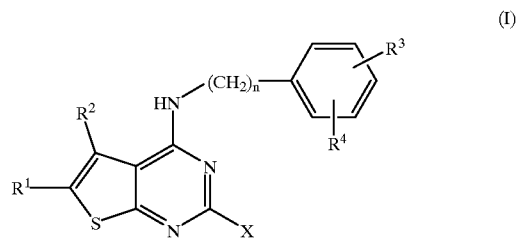

(I)

wherein $R_1$ and $R_2$ are independently selected from the group consisting of hydrogen, A, OA, alkenyl, alkynyl, $-NO_2$, $-CF_3$ or halogen, with the proviso that one of $R_1$ or $R_2$ is not hydrogen; or $R_1$ and $R_2$ together form a $C_{3-5}$ alkylene group;

$R_3$ and $R_4$ are independently selected from the group consisting of hydrogen, A, $-OA$, halogen, $-NO_2$, $-NH_2$, $-NHA$ or $-NAA'$, or $R_3$ and $R_4$ are together form a moiety selected from the group consisting of $-O-CH_2-CH_2-$, $-O-CH_2-O-$ or $-CH_2-CH_2-O$, X is selected from the group consisting of a substituted 5–7 membered saturated heterocyclic ring or a substituted saturated or saturated isocyclic ring, wherein the substitutents on the "X" ring are one or two selected from the group consisting of $-COOH$, $-COOA$, $-CONH_2$, $-CONAA'$, $-CONHA$, $-CN$, $-CH_2COOH$ or $-CH_2CH_2COOH$;

A and A' are independently selected from the group consisting of hydrogen or $C_{1-6}$ alkyl; and n is 0, 1, 2 or 3; and physiologically acceptable salts thereof.

8. The method of claim 7 wherein X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH.

9. The method of claim 8 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; and n is 1.

10. The method of claim 8 wherein $R_3$ and $R_4$ are independently selected from the group consisting of hydrogen, A, OA, halogen, —NO$_2$, —NH$_2$, —NHA or —NAA'; and n is 1.

11. The method of claim 8 wherein $R_1$ and $R_2$ together form a $C_{3-5}$ alkylene; $R_3$ and $R_4$ together form a moiety selected from the group consisting of —O—CH$_2$—CH$_2$—, —O, —CH$_2$—O— or —O—CH$_2$—CH$_2$—O; and n is 1.

12. The method of claim 8 wherein $R_1$ and $R_2$ together form a $C_{3-5}$ alkylene; $R_3$ and $R_4$ are independently selected from the group consisting of hydrogen, A, OA, halogen, NO$_2$, —NH$_2$, NHA or NAA'; and n is 1.

13. A method for regulating apoptosis in human cells comprising exposing said cells to an effective amount of a compound of the formula:

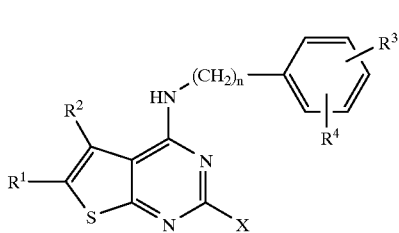

(I)

wherein $R_1$ and $R_2$ are independently selected from the group consisting of hydrogen, A, OA, alkenyl, alkynyl, —NO$_2$, —CF$_3$ or halogen, with the proviso that one of $R_1$ or $R_2$ is not hydrogen; or $R_1$ and $R_2$ together form a $C_{3-5}$ alkylene group;

$R_3$ and $R_4$ are independently selected from the group consisting of hydrogen, A, —OA, halogen, —NO$_2$, —NH$_2$, —NHA or —NAA', or $R_3$ and $R_4$ are together form a moiety selected from the group consisting of —O—CH$_2$—CH$_2$—, —O—CH$_2$—O— or —O—CH$_2$—CH$_2$—O;

X is selected from the group consisting of a substituted 5-7 membered saturated heterocyclic ring or a substituted saturated or saturated isocyclic ring, wherein the substitutents on the "X" ring are one or two selected from the group consisting of —COOH, —COOA, —CONH$_2$, —CONAA', —CONHA, —CN, —CH$_2$COOH or —CH$_2$CH$_2$COOH;

A and A' are independently selected from the group consisting of hydrogen or $C_{1-6}$ alkyl; and n is 0, 1, 2 or 3; and physiologically acceptable salts thereof.

14. The method of claim 13 wherein X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH.

15. The method of claim 14 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; and n is 1.

16. The method of claim 14 wherein $R_3$ and $R_4$ are independently selected from the group consisting of hydrogen, A, OA, halogen, —NO$_2$, —NH$_2$, —NHA or —NAA'; and n is 1.

17. The method of claim 14 wherein $R_1$ and $R_2$ together form a $C_{3-5}$ alkylene; $R_3$ and $R_4$ together form a moiety selected from the group consisting of —O—CH$_2$—CH$_2$—, —O, —CH$_2$—O— or —O—CH$_2$—CH$_2$—O; and n is 1.

18. The method of claim 14 wherein $R_1$ and $R_2$ together form a $C_{3-5}$ alkylene; $R_3$ and $R_4$ are independently selected from the group consisting of hydrogen, A, OA, halogen, NO$_2$, NH$_2$, NHA or NAA'; and n is 1.

19. The method of claim 1 wherein said compound is selected from the group consisting of:

4-[4-(3,4-Methylenedioxy-benzylamino)-5,6,7,8-tetrahydro-[1]-benzothieno-[2,3-d]-pyrimidin-2yl]-benzoic acid;

4-[4-(3,4-Methylenedioxy-benzylamino)-6-methyl-thieno-[2,3-d]pyrimidin-2-yl]-benzoic acid;

4-[4-(3,4-Methylenedioxy-benzylamino)-5,6-dimethyl-thieno[2,3-d]-pyrimidin-2-yl]-benzoic acid;

4-[4-(3,4-Methylenedioxy-benzylamino)-6-chloro-thieno-[2,3-d]-pyrimidin-2-yl]-benzoic acid;

4-[4-(3-Chloro-4-methoxy-benzylamino)-5,6,7,8-tetrahydro-[1]-benzothieno-[2,3-d]-pyrimidin-2-yl]-benzoic acid;

1-[4-(3,4-Methylenedioxy-benzylamino)-5,6,7,8-tetrahydro-[1]-benzothieno-[2,3-d]-pyrimidin-2-yl]-piperidinyl-4-carboxylic acid;

1-[4-(3,4-Methylenedioxy-benzylamino)-6-methyl-thieno-[2,3-d]-pyrimidin-2-yl]-piperidinyl-4-carboxylic acid; and 4-[4(3,4-Methylenedioxy-benzylamino)-5,6,7,8-tetrahydro-[1]-benzothieno-[2,3-d]-pyrimidin-2-yl-]-cyclohexancarboxylic acid.

* * * * *